(12) United States Patent
Westermarck et al.

(10) Patent No.: US 9,476,050 B2
(45) Date of Patent: Oct. 25, 2016

(54) COMBINATION THERAPY

(75) Inventors: Jukka Westermarck, Turku (FI); John Eriksson, Turku (FI); Amanpreet Kaur, Turku (FI); Emilia Peuhu, Turku (FI)

(73) Assignee: TURUN YLIOPISTO, Turun Yliopisto (FI)

( * ) Notice: Subject to any disclaimer, the term of this patent is extended or adjusted under 35 U.S.C. 154(b) by 0 days.

(21) Appl. No.: 14/128,342

(22) PCT Filed: Jun. 15, 2012

(86) PCT No.: PCT/FI2012/050618
§ 371 (c)(1),
(2), (4) Date: Jan. 17, 2014

(87) PCT Pub. No.: WO2012/175798
PCT Pub. Date: Dec. 27, 2012

(65) Prior Publication Data
US 2014/0135377 A1    May 15, 2014

Related U.S. Application Data

(60) Provisional application No. 61/499,750, filed on Jun. 22, 2011.

(30) Foreign Application Priority Data

Jun. 22, 2011  (FI) .................................... 20115640

(51) Int. Cl.
| | |
|---|---|
| *C12N 15/113* | (2010.01) |
| *A61K 31/553* | (2006.01) |
| *A61K 31/713* | (2006.01) |
| *A61K 45/06* | (2006.01) |
| *A61K 31/5513* | (2006.01) |
| *A61K 31/551* | (2006.01) |

(52) U.S. Cl.
CPC ......... *C12N 15/1137* (2013.01); *A61K 31/551* (2013.01); *A61K 31/553* (2013.01); *A61K 31/5513* (2013.01); *A61K 31/713* (2013.01); *A61K 45/06* (2013.01); *C12N 15/1135* (2013.01); *C12N 2310/14* (2013.01); *C12N 2320/31* (2013.01)

(58) Field of Classification Search
None
See application file for complete search history.

(56) References Cited

U.S. PATENT DOCUMENTS

| | | | |
|---|---|---|---|
| 6,300,492 B1* | 10/2001 | Korneluk et al. ........... | 536/24.5 |
| 2003/0143732 A1 | 7/2003 | Fosnaugh et al. | |
| 2003/0148507 A1 | 8/2003 | Fosnaugh et al. | |
| 2003/0175950 A1 | 9/2003 | McSwiggen | |
| 2003/0190635 A1 | 10/2003 | McSwiggen | |
| 2004/0019001 A1 | 1/2004 | McSwiggen | |
| 2004/0077083 A1 | 4/2004 | Watt | |
| 2004/0077084 A1 | 4/2004 | Watt et al. | |
| 2005/0008617 A1 | 1/2005 | Chen et al. | |
| 2005/0043266 A1 | 2/2005 | Jayasena et al. | |
| 2005/0245475 A1 | 11/2005 | Khvorova et al. | |
| 2005/0255487 A1 | 11/2005 | Khvorova et al. | |
| 2009/0182134 A1* | 7/2009 | Khvorova et al. ........... | 536/23.1 |
| 2009/0239244 A1 | 9/2009 | Shi et al. | |
| 2010/0184820 A1* | 7/2010 | Valent ........................ | 514/44 A |

FOREIGN PATENT DOCUMENTS

| | | |
|---|---|---|
| WO | WO 00/20432 A1 | 4/2000 |
| WO | WO 2004/017991 A1 | 3/2004 |
| WO | WO 2004/045543 A2 | 6/2004 |
| WO | WO 2004/096991 A2 | 11/2004 |
| WO | WO 2005/011598 A2 | 2/2005 |
| WO | WO 2006/010628 A1 | 2/2006 |
| WO | WO 2007/174613 A2 | 12/2007 |
| WO | WO 2009/100173 A2 | 8/2009 |
| WO | WO 2010/091140 A1 | 8/2010 |

OTHER PUBLICATIONS

Afanas'ev et al., "Flow cytometry and biochemical analysis of DNA degradation characteristic of two types of cell death," FEBS 3228, vol. 194, No. 2, Jan. 1986, pp. 347-350.
Cui et al., "OptiRNAi, an RNAi design tool," Computer Methods and Programs in Biomedicine, vol. 75, 2004, pp. 67-73.
Deng et al., "Survival function of ERK1/2 as IL-3-activated staurosporine-resistant Bcl2 kinases," PNAS, vol. 97, No. 4, Feb. 15, 2000, pp. 1578-1583, XP002907019.
Janssens et al., "PP2A holoenzyme assembly: in cauda venenum (the sting is in the tail)," Trends in Biochem. Sci., vol. 33, No. 3, 2008, pp. 113-121.
Kim et al., "Synthetic dsRNA Dicer substrates enhance RNAi potency and efficacy," Nature Biotechnology, vol. 23, No. 2, Feb. 2005 (published online Dec. 26, 2004), pp. 222-226.
Li et al., "Ribozyme Technology for Cancer Gene Target Identification and Validation," Advances in Cancer Research, 2007, pp. 103-143.
McCubrey et al., "Roles of the Raf/MEK/ERK pathway in cell growth, malignant transformation and drug resistance," Biochimica et Biophysica Acta, vol. 1773, 2007 (available online Oct. 7, 2006), pp. 1263-1284, XP022181679.
Mumby, "PP2A: Unveiling a Reluctant Tumor Suppressor," Cell, vol. 130, Jul. 13, 2007, pp. 21-24.
Prosperi et al., "Nuclease-Induced DNA Structural Changes Assessed by Flow Cytometry With the Intercalating Dye Propidium Iodide 1,2," Cytometry, vol. 12, 1991, pp. 323-329.
Puustinen et al., "PME-1 Protects Extracellular Signal-Regulated Kinase Pathway Activity from Protein Phosphatase 2A-Mediated Inactivation in Human Malignant Glioma," Cancer Res, vol. 69, 2009, (published online first Mar. 17, 2009), pp. 2870-2877, XP055042881.

(Continued)

*Primary Examiner* — Tracy Vivlemore
(74) *Attorney, Agent, or Firm* — Birch, Stewart, Kolasch & Birch, LLP

(57) ABSTRACT

The invention is based on a finding that silencing PME-1 gene sensitizes cancer cells for apoptosis-inducing activity of certain small molecule chemotherapeutic agents. Thus, the invention is directed to a respective combination therapy, sensitization method and pharmaceutical compositions.

17 Claims, 10 Drawing Sheets

(56) References Cited

OTHER PUBLICATIONS

Riccardi et al., "Analysis of apoptosis by propidium iodide staining and flow cytometry," Nature Protocols, vol. 1, No. 3, 2006, (published online Nov. 9, 2009), pp. 1458-1461.

Sontag et al., "Folate Deficiency Induces In Vitro and Mouse Brain Region-Specific Downregulation of Leucine Carboxyl Methyltransferase-1 and Protein Phosphatase 2A Bα Subunit . . . ," The Journal of Neuroscience, vol. 28, No. 45, Nov. 5, 2008, pp. 11477-11487.

Vassilev et al., "In Vivo Activation of the p53 Pathway by Small-Molecule Antagonists of MDM2," Science, vol. 303, 2004, pp. 844-848.

Westermarck et al., "Multiple pathways regulated by the tumor suppressor PP2A in transformation," Trends in Molecular Medicine, vol. 14, No. 4, 2008, (available online Mar. 10, 2008), pp. 152-160.

Xing et al., "Structural Mechanism of Demethylation and Inactivation of Protein Phosphatase 2A," Cell, vol. 133, Apr. 4, 2008, pp. 154-163.

Zhao et al., "Functional genetics and experimental models of human cancer," Trends in Molecular Medicine, vol. 10, No. 7, Jul. 2004, (available online Jun. 17, 2004), pp. 344-350.

Basile et al., "DNA Damage Promotes Histone Deacetylase 4 Nuclear Localization and Repression of G2/M Promotes, via p53 C-terminal Lysines," Journal of Biological Chemistry, vol. 281, No. 4, Jan. 2006, pp. 2347-2357.

Chen et al., "CHK1 Inhibition as a Strategy for Targeting Fanconi Anemia (FA) DNA Repair Pathway Deficient Tumors," Molecular Cancer, vol. 8, No. 24, Apr. 2009, pp. 1-16.

Chen et al., "HDAC4 Regulates Neuronal Survival in Normal and Diseased Retinas," Science, vol. 323, Jan. 2009, pp. 256-259.

Finish Office Action dated May 7, 2013 for Finish Patent Application No. 20122795.

Finish Search Report dated May 7, 2013 for Finish Patent Application No. 20125795.

Geng et al., "HDAC4 Protein Regulates HIF1a Protein Lysine Acetylation and Cancer Cell Response to Hypoxia," Journal of Biological Chemistry, vol. 286, No. 44, Nov. 2011, pp. 38095-38102.

Li et al., "Nuclear Accumulation of HDAC4 in ATM Defiency Promotes Neurodegeneration in Ataxia Telangiectasia," Nature Medicine, vol. 18, No. 5, May 2012, pp. 783-791.

Lin et al., "Functional Dissection of Lysine Deacetylases Reveals that HDAC1 and p300 Regulate AMPK." Nature, vol. 482, Feb. 2012, pp. 251-258.

Liu et al., "FOXP3 Up-regulates p21 Expression by Site-Specific Inhibition of Histone Deacetylase2/Histone Deacetylase 4 Association to the Locus," Cancer Research, vol. 69, 2009, pp. 2252-2259.

Majdzadeh et al., "Class IIA HDACS in the Regulation of Neurodegeneration," Front Biosci., vol. 13, Jun. 2009, pp. 1072-1082.

Mottet et al., "HDAC4 Represses p21 WAF1/Cipl Expression in Human Cancer Cells Through a Sp1-Dependent, p53-Independent Mechanism," Ocogene, vol. 28, 2009, pp. 243-256.

Parra et al., "Regulatory Signal Transduction Pathways for Class IIA Histone Deacetylases," Current Opinion in Pharmacology, vol. 10, 2010, pp. 454-460.

Stronach et al., "HDAC4-Regulated STAT1 Activation Mediates Platinum Resistance in Ovarian Cancer," Cancer Research, vol. 71, No. 13, Jul. 2011, pp. 4412-4422.

Wilson et al., "HDAC4 Promotes Growth of Colon Cancer Cells via Repression of p21," Molecular Biology of the Cell, vol. 19, Oct. 2008, pp. 4062-4075.

Witt et al., "HDAC family: What are the cancer relevant targets?," Cancer Letters, vol. 277, 2009, pp. 8-21.

Yao et al., "Beyong Histone and Deacetylase: An Overview of Cytoplasmic Histone Deacetylaes and Their Nonhistone Substrates," Journal of Biomedicine and Biotechnology, 2011, pp. 1-15.

\* cited by examiner

SEQUENCE LISTING

```
<160> NUMBER OF SEQ ID NOS: 46

<210> SEQ ID NO 1
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 1
ggaagugagu cuauaagca                                                       19

<210> SEQ ID NO 2
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 2
ucauagagga agaagaaga                                                       19

<210> SEQ ID NO 3
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 3
aggucaagaa uccugaaga                                                       19

<210> SEQ ID NO 4
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 4
acagugugaa ggaauuaca                                                       19

<210> SEQ ID NO 5
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 5
ucuauagugg aaggaauca                                                       19
```

```
<210> SEQ ID NO 6
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 6
gguacagcua uggaugcac                                                  19

<210> SEQ ID NO 7
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 7
ggaaggaauc auagaggaa                                                  19

<210> SEQ ID NO 8
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 8
ggccaaagcc uauggaauu                                                  19

<210> SEQ ID NO 9
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 9
auguagaagu agagaauga                                                  19

<210> SEQ ID NO 10
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 10
ggucaagaau ccugaagau                                                  19

<210> SEQ ID NO 11
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 11
cugcagaaac aauggcaaa                                                  19

<210> SEQ ID NO 12
<211> LENGTH: 19
<212> TYPE: RNA
<213> ORGANISM: Artificial Sequence
<220> FEATURE:
<223> OTHER INFORMATION: PME-1 siRNA
```

```
<400> SEQUENCE: 12
gcgaagucau ggugaaaca                                                   19

<210> SEQ ID NO 13
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 13
cauggaagau guagaagua                                                   19

<210> SEQ ID NO 14
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 14
agaagaagaa gaugaggaa                                                   19

<210> SEQ ID NO 15
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 15 gcgaugggc ccuggaaga                                                    19

<210> SEQ ID NO 16
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 16
aggaagaaga agaagauga                                                   19

<210> SEQ ID NO 17
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 17
agauguagaa guagagaau                                                   19

<210> SEQ ID NO 18
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 18
ucuauaagca agaggaaaa                                                   19
```

```
<210> SEQ ID NO 19
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 19
aaucauagag gaagaagaa                                                  19

<210> SEQ ID NO 20
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 20
ggguaaagcc uccagauuu                                                  19

<210> SEQ ID NO 21
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 21
caaacagugu gaaggaauu                                                  19

<210> SEQ ID NO 22
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 22
ggagaauuga acuggcaaa                                                  19

<210> SEQ ID NO 23
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 23
ucauagagga agaagaaga                                                  19

<210> SEQ ID NO 24
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 24
gcuauugaau ggaguguga                                                  19

<210> SEQ ID NO 25
<211> LENGTH: 19
<212> TYPE: RNA
<213> ORGANISM: Artificial Sequence
<220> FEATURE:
<223> OTHER INFORMATION: PME-1 siRNA
```

```
<400> SEQUENCE: 25
cuuaauagca ugcagaauu                                              19

<210> SEQ ID NO 26
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 26
gaaugaaacu ggcaaggau                                              19

<210> SEQ ID NO 27
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 27
aagaugacau ggagaccaa                                              19

<210> SEQ ID NO 28
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 28
uggaagaugu agaaguaga                                              19

<210> SEQ ID NO 29
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 29
aaggaaucau agaggaaga                                              19

<210> SEQ ID NO 30
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 30
aaucuauagu ggaaggaau                                              19

<210> SEQ ID NO 31
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 31
ccaagaaaga ccauccaua                                              19
```

```
<210> SEQ ID NO 32
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 32
caugauugau guuguagaa                                                19

<210> SEQ ID NO 33
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 33
guggauagca ucacaagaa                                                19

<210> SEQ ID NO 34
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 34
cauagaggaa gaagaagaa                                                19

<210> SEQ ID NO 35
<211> LENGTH: 19
<212> TYPE: RNA
<213> ORGANISM: Artificial Sequence
<220> FEATURE:
<223> OTHER INFORMATION: PME-1 siRNA

<400> SEQUENCE: 35
gaacaaaggu caagaaucc                                                19

<210> SEQ ID NO 36
<211> LENGTH: 21
<212> TYPE: DNA
<213> ORGANISM: Artificial Sequence
<220> FEATURE:
<223> OTHER INFORMATION: PME-1 siRNA

<400> SEQUENCE: 36
ctggtgttga tagattggat a                                             21

<210> SEQ ID NO 37
<211> LENGTH: 21
<212> TYPE: DNA
<213> ORGANISM: Artificial Sequence
<220> FEATURE:
<223> OTHER INFORMATION: PME-1 shRNA

<400> SEQUENCE: 37
ctggtgttga tagattggat a                                             21

<210> SEQ ID NO 38
<211> LENGTH: 21
<212> TYPE: DNA
<213> ORGANISM: Artificial Sequence
<220> FEATURE:
<223> OTHER INFORMATION: PME-1 shRNA
```

```
<400> SEQUENCE: 38
cccaggttaa atacagccca t                                              21

<210> SEQ ID NO 39
<211> LENGTH: 21
<212> TYPE: DNA
<213> ORGANISM: Artificial Sequence
<220> FEATURE:
<223> OTHER INFORMATION: PME-1 shRNA

<400> SEQUENCE: 39
gcttatccaa tctctttctt a                                              21

<210> SEQ ID NO 40
<211> LENGTH: 19
<212> TYPE: RNA
<213> ORGANISM: Artificial Sequence
<220> FEATURE:
<223> OTHER INFORMATION: Scrambled siRNA

<400> SEQUENCE: 40
guaacaauga gagcacggc                                                 19

<210> SEQ ID NO 41
<211> LENGTH: 18
<212> TYPE: RNA
<213> ORGANISM: Artificial Sequence
<220> FEATURE:
<223> OTHER INFORMATION: CIP2A siRNA

<400> SEQUENCE: 41
cugugguugu guuugcac                                                  18

<210> SEQ ID NO 42
<211> LENGTH: 18
<212> TYPE: RNA
<213> ORGANISM: Artificial Sequence
<220> FEATURE:
<223> OTHER INFORMATION: PPP2R2A siRNA

<400> SEQUENCE: 42
cugcagauga uuugcgga                                                  18

<210> SEQ ID NO 43
<211> LENGTH: 21
<212> TYPE: RNA
<213> ORGANISM: Artificial Sequence
<220> FEATURE:
<223> OTHER INFORMATION: PPP2AR2C siRNA

<400> SEQUENCE: 43
accgcucauu cuucucggaa a                                              21

<210> SEQ ID NO 44
<211> LENGTH: 19
<212> TYPE: RNA
<213> ORGANISM: Artificial Sequence
<220> FEATURE:
<223> OTHER INFORMATION: PPP2R3B siRNA

<400> SEQUENCE: 44
cacgugucuc ugucacgug                                                 19
```

```
<210> SEQ ID NO 45
<211> LENGTH: 19
<212> TYPE: RNA
<213> ORGANISM: Artificial Sequence
<220> FEATURE:
<223> OTHER INFORMATION: PPP2R5A siRNA

<400> SEQUENCE: 45
cuguaucaug gccauagua                                                  19

<210> SEQ ID NO 46
<211> LENGTH: 19
<212> TYPE: RNA
<213> ORGANISM: Artificial Sequence
<220> FEATURE:
<223> OTHER INFORMATION: PPP2R5B siRNA

<400> SEQUENCE: 46
ccgcaugauc ucagugaau                                                  19
```

COMBINATION THERAPY

CROSS-REFERENCE TO THE RELATED APPLICATIONS

This application is the National Phase of PCT/FI2012/050618 filed on Jun. 15, 2012, which claims priority under 35 U.S.C. 119(e) to U.S. Provisional Application No. 61/499,750 filed on Jun. 22, 2011 and under 35 U.S.C. 119(a) to Patent Application No. 20115640 filed on Jun. 22, 2011 in Finland, all which are hereby expressly incorporated by reference into the present application.

FIELD OF THE INVENTION

This invention relates to the field of combination cancer therapeutics.

BACKGROUND OF THE INVENTION

Cancer is a devastating disease afflicting all communities worldwide. It has been estimated that 1 out of 2 men and 1 out 3 women will develop some form cancer within their lifetime.

Interestingly, it has been recently established that, regardless of the phenotypic variability between different cancer types, perturbation of limited number of genetic elements is sufficient to induce cellular transformation in many different human cell types (reviewed in Zhao et al., Trends Mol Med, 2004, 10: 344-350). Experimentally, it was demonstrated that activation of Ras and telomerase (TERT), along with inactivation of the tumor suppressor proteins p53 and Retinoblastoma protein (Rb) can immortalize a variety of human cell types, which can subsequently transform to a tumorigenic state in response to inhibition of protein phosphatase 2A (PP2A) (Mumby, Cell, 2007, 130(1):21-24; Westermarck and Hahn, Trends Mol. Med., 2008, 14(4): 152-160; Zhao et al., Trends Mol Med, 2004, 10: 344-350). Therefore, these common genetic elements could be considered as master regulators of cancer development (Zhao et al., Trends Mol Med, 2004, 10: 344-350).

PP2A is a widely conserved protein serine/threonine phosphatase (PSP) that functions as a trimeric protein complex consisting of a catalytic subunit (PP2Ac or C), a scaffold subunit (PR65 or A), and one of the alternative regulatory B subunits. As described above, recent experimental evidence has firmly established that inhibition of PP2A activity is a prerequisite for human cell transformation (reviewed in Westermarck and Hahn, Trends Mol. Med., 2008, 14(4):152-160). Nevertheless, very little is known about mechanisms regulating PP2A complex composition and/or activity in vivo. Identification of PP2A inhibiting mechanisms might provide opportunities for development of novel class of cancer therapeutics re-activating PP2A tumor suppressor activity. This idea would be similar to cancer therapy approaches aiming at re-activation of tumor suppressor activity of p53 by small-molecules such as Nutlin-3 (Vassilev et al., Science, 2004, 303:844-48).

Protein phosphatase methylesterase 1 (PME-1) has been identified as a cancer-associated PP2A-interacting protein (Puustinen et al., Cancer Res., 2009, 69:2870-2877). Earlier biochemical studies had established PME-1 as a protein that inhibits PP2A activity via its enzymatic methylesterase activity required for demethylation of the conserved leucine 309 on catalytic PP2Ac subunit (Janssens et al., Trends Biochem. Sci., 2008, 33:113-21). An alternative mechanism by which PME-1 inhibits PP2A activity was proposed by structural analysis of PME-1-PP2A complex demonstrating that PME-1 directly binds to catalytic cleft of the PP2Ac subunit (Xing et al., Cell, 2008, 133:154-163). However, the functional relevance of PME-1 or its role in regulation of cellular signaling had not been addressed. PME-1 expression has been reported to correlate with human glioblastoma (GBM) progression, and with proliferation, as well as ERK MAPK pathway activity in human patient samples of GBM. Experimentally it was shown that PME-1 inhibition by siRNA inhibited ERK pathway activity and malignant cell growth (Puustinen et al., Cancer Res., 2009, 69:2870-2877). However, loss of PME-1 did not induce efficient cell death regardless of its potent effects on inhibition of malignant cell growth (Puustinen et al., Cancer Res., 2009, 69:2870-2877).

Cell killing and/or apoptosis are the preferable endpoints for cancer therapy regimens. On the other hand, either intrinsic or acquired resistance is the major problem related to currently used chemotherapies. Thus, although at least some of the mechanisms underlying malignancy have been revealed, there exists a need in the art for the development of medicaments for hyperproliferative diseases and especially cancer.

BRIEF DESCRIPTION OF THE INVENTION

The present invention is based on a surprising, synergistic effect of PME-1 gene silencing and certain small molecule chemical agents on the level of apoptosis in hyperproliferative cells.

Thus, in one aspect, the invention provides a combination of PME-1 silencing and a chemical compound having a general Formula (I):

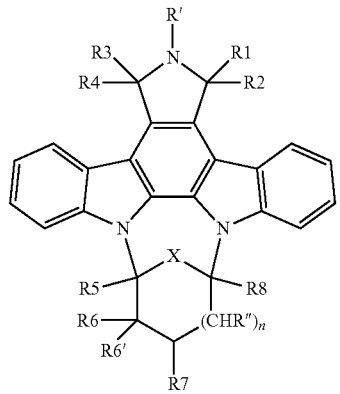

R' is H or alkyl;
R" is H or alkoxy;
R1 and R2 are H or together form oxo;
R3 and R4 are independently H, OH or together form oxo:
R5, R6, R6', R7, and R8 are independently selected from the group consisting of H, alkyl, alkoxy, hydroxy, hydroxylalkyl, alkoxycarbonyl, or mono- and dialkylamino;
X is CH$_2$ or O; and
n is 0 or 1, as medicine.

In another aspect, the invention provides a small double-stranded RNA (dsRNA) molecule comprising a nucleic acid sequence selected from the group consisting of SEQ ID NO:s 3 to 5.

In a further aspect, the invention provides a pharmaceutical composition comprising the above-mentioned combination or dsRNA.

In a still further aspect, the invention provides a method of sensitizing hyperproliferative cells to a chemotherapeutic agent by silencing PME-1 gene in a human or animal subject in need of such sensitization.

Furthermore, one aspect of the invention provides method of treating a hyperproliferative disease in a human or animal subject in need of such treatment by administering at least one type of PME-1 silencing agent and a compound of Formula (I) as defined above.

In some embodiments of the above aspects, said PME-1 silencing is obtained by an agent selected from the group consisting of an siRNA molecule, DsiRNA molecule, artificial miRNA precursor, shRNA molecule, antisense oligonucleotide, ribozyme, agent preventing PME-1 function towards PP2Ac, and any combinations thereof. In further embodiments, the PME-1 silencing agent comprises a nucleic acid sequence selected from the group consisting of SEQ ID NO:s 1 to 39.

In some embodiments of the above aspects, the hyperproliferative disease to be treated is selected from a group consisting of psoriasis, myocardial hypertrophy, benign tumors, solid cancers and haematological cancers. Non-limiting examples of said solid cancers include squamous cell carcinomas of the head and neck, colon cancer, gastric cancer, breast cancer, ovarian cancer, prostate cancer, cervical cancer, brain cancer, glioma, astrocytoma, and glioblastoma.

Other specific embodiments, objects, details, and advantages of the invention are set forth in the dependent claims, following drawings, detailed description and examples.

BRIEF DESCRIPTION OF THE DRAWINGS

In the following the invention will be described in greater detail by means of preferred embodiments with reference to the attached drawings, in which

FIG. 5B represent the colonogenic potential of scrambled or PME-1 specific dsRNA transfected T98G glioblastoma cells after 2 days of treatment with indicated concentration of staurosporine analogues, PKC412 and K252a.

FIGS. 5C and 5D represent the colonogenic potential of scrambled or PME-1 specific dsRNA transfected U251MG and U87MG glioblastoma cells respectively, after 2 days of treatment with indicated concentration of staurosporine (STS), PKC412 and K252a.

DETAILED DESCRIPTION OF THE INVENTION

Figure 1A:
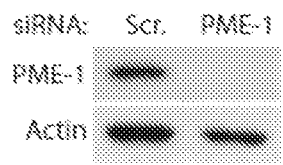
FIG. 1A is a western blot demonstrating PME-1 silencing activity of a scrambled dsRNA (Scr.) and PME-1 specific dsRNA (PME-1) in human glioblastoma T98G cells.

The present invention is based on a surprising finding that silencing PME-1 gene sensitizes cancer cells for apoptosis-inducing activity of certain small molecule chemotherapeutic agents. Concomitant silencing of PME-1 gene and administration of said chemotherapeutic agent results in synergistic increase in the level of apoptosis. Thus, in one aspect, the invention provides a combination therapy of PME-1 depletion and said chemotherapeutic agents.

PME-1 gene silencing may be obtained by any suitable method known in the art including, but not limited to, RNA interference (RNAi). The most common approach for RNAi-based gene silencing is the use of small interfering RNA (siRNA).

The principle of siRNA is extensively presented in literature. As examples can be mentioned the US patent publications 2003/0143732, 2003/0148507, 2003/0175950, 2003/0190635, 2004/0019001, 2005/0008617 and 2005/0043266. An siRNA duplex molecule comprises an antisense region and a sense strand wherein said antisense strand comprises sequence complementary to a target region in an mRNA sequence encoding a certain protein, and the sense strand comprises sequence complementary to the said antisense strand. Thus, the siRNA duplex molecule is assembled from two nucleic acid fragments wherein one fragment comprises the antisense strand and the second fragment comprises the sense strand of said siRNA molecule. In other words, siRNAs are small double-stranded RNAs (dsRNAs). The sense strand and antisense strand can be covalently connected via a linker molecule, which can be a polynucleotide linker or a non-nucleotide linker. The length of the antisense and sense strands may vary and is typically about 19 to 21 nucleotides each. In some cases, the siRNA may comprise 22, 23 or 24 nucleotides.

Another approach for RNAi-based PME-1 silencing is to use longer, typically 25-35 nt, Dicer substrate siRNAs (DsiRNAs), which in some cases have been reported to be more potent than corresponding conventional 21-mer siRNAs (Kim et al., Nat Biotechol, 2005, 23: 222-226). DsiRNAs are processed in vivo into active siRNAs by Dicer.

In a cell, an active siRNA antisense strand is formed and it recognizes a target region of the target mRNA. This in turn leads to cleaving of the target RNA by the RISC endonuclease complex (RISC=RNA-induced silencing complex) and also in the synthesis of additional RNA by RNA dependent RNA polymerase (RdRP), which can activate Dicer and result in additional siRNA duplex molecules, thereby amplifying the response.

As used herein, the term "dsRNA" refers to both siRNAs and DsiRNAs.

Typically, but not necessarily, the antisense strand and the sense strand of dsRNA both comprise a 3'-terminal overhang of a few, typically 1 to 3 nucleotides. The 3' overhang may include one or more modified nucleotides, such as a 2'-O-methyl ribonucleotide. The 5'-terminal of the antisense is typically a phosphate group (P). The dsRNA duplexes having terminal phosphate groups (P) are easier to administrate into the cell than a single stranded antisense. In some cases, the 5'-terminal of the sense strand or of both antisense and sense strands may comprise a P group.

Normal, unmodified RNA has low stability under physiological conditions because of its degradation by ribonuclease enzymes present in the living cell. If the oligonucleotide shall be administered exogenously, it is highly desirable to modify the molecule according to known methods so as to enhance its stability against chemical and enzymatic degradation.

Modifications of nucleotides to be administered exogenously in vivo are extensively described in the art (e.g. in US 2005/0255487, incorporated herein by reference). Principally, any part of the nucleotide, i.e the ribose sugar, the base and/or internucleotidic phosphodiester strands can be modified. For example, removal of the 2'-OH group from the ribose unit to give 2'-deoxyribosenucleotides results in improved stability. Prior disclosed are also other modifications at this group: the replacement of the ribose 2'-OH group with alkyl, alkenyl, allyl, alkoxyalkyl, halo, amino, azido or sulfhydryl groups. Also other modifications at the ribose unit can be performed: locked nucleic acids (LNA) containing methylene linkages between the 2'- and 4'-positions of the ribose can be employed to create higher intrinsic stability.

Furthermore, the internucleotidic phosphodiester linkage can, for example, be modified so that one or more oxygen is replaced by sulfur, amino, alkyl or alkoxy groups. Also the base in the nucleotides can be modified.

Preferably, the oligonucleotide comprises modifications of one or more 2'-hydroxyl groups at ribose sugars, and/or modifications in one or more internucleotidic phosphodiester linkages, and/or one or more locked nucleic acid (LNA) modification between the 2'- and 4'-position of the ribose sugars.

Particularly preferable modifications are, for example, replacement of one or more of the 2'-OH groups by 2'-deoxy, 2'-O-methyl, 2'-halo, e.g. fluoro or 2'-methoxyethyl. Especially preferred are oligonucleotides where some of the internucleotide phoshodiester linkages also are modified, e.g. replaced by phosphorothioate linkages.

In some embodiments, dsRNAs may contain one or more synthetic or natural nucleotide analogs including, but not limited to, phosphorothioates, phosphoramidates, methyl phosphonates, chiral-methyl phosphonates, and peptide-nucleic acids (PNAs) as long as dsRNAs retain their PME-1 silencing ability.

It should be stressed that the modifications mentioned above are only non-limiting examples.

One of the challenges related to RNAi is the identification of a potent dsRNA for the corresponding mRNA. It should be noted that genes with incomplete complementarity are inadvertently downregulated by the dsRNA, leading to problems in data interpretation and potential toxicity. This however can be partly addressed by carefully designing appropriate dsRNAs with design algorithms. These computer programs sieve out given target sequence with a set of rules to find sequence stretches with low GC content, a lack of internal repeats, an A/U rich 5-end and high local free binding energy which are features that enhance the silencing effect of dsRNA.

In order to identify agents useful in the present invention, several different PME-1 siRNAs were designed by using commercial and non-commercial algorithms. To this end, full length cDNA sequence of PME-1 was loaded to siRNA algorithm programs (Eurofins MWG Operon's Online Design Tool) and stand-alone program developed by Cuia et al. (Biomedicine, 2004, 75: 67-73). Further, algorithm generated siRNA sequences were then screened trough genome wide DNA sequence alignment (BLAST) to eliminate siRNAs which are not free from off-targeting. In other words, all those siRNAs which had even short sequence regions matching with other genes than target gene (PME-1) were considered invaluable for further use.

Obtained siRNAs were then transfected to different cell lines and their capacity to degrade mRNA and further deplete translation of PME-1 was studied at protein level by measuring the amount of PME-1 protein after siRNA treatment with PME-1 specific antibodies (Table 1).

TABLE 1

PME-1 specific siRNAs

| SEQ ID NO | siRNA sense sequence (5' to 3') | % PME-1 inhibition (protein level) |
|---|---|---|
| 1 | GGA AGU GAG UCU AUA AGC A | >90% |
| 2 | UCA UAG AGG AAG AAG AAG A | >55% |
| 3 | AGG UCA AGA AUC CUG AAG A | >84% |
| 4 | ACA GUG UGA AGG AAU UAC A | >85% |
| 5 | UCU AUA GUG GAA GGA AUC A | >80% |
| 6 | GGU ACA GCU AUG GAU GCA C | 64% |

Further PME-1 specific siRNAs suitable for use in various embodiments of the present invention have been disclosed in US 2009/182134 and are listed in Table 2.

TABLE 2

Further PME-1 specific siRNAs

| SEQ ID NO | siRNA sense sequence (5' to 3') |
|---|---|
| 7 | GGAAGGAAUCAUAGAGGAA |
| 8 | GGCCAAAGCCUAUGGAAUU |
| 9 | AUGUAGAAGUAGAGAAUGA |
| 10 | GGUCAAGAAUCCUGAAGAU |
| 11 | CUGCAGAAACAAUGGCAAA |
| 12 | GCGAAGUCAUGGUGAAACA |
| 13 | CAUGGAAGAUGUAGAAGUA |
| 14 | AGAAGAAGAAGAUGAGGAA |
| 15 | GCGAAUGGGCCCUGGAAGA |
| 16 | AGGAAGAAGAAGAAGAUGA |
| 17 | AGAUGUAGAAGUAGAGAAU |
| 18 | UCUAUAAGCAAGAGGAAAA |
| 19 | AAUCAUAGAGGAAGAAGAA |
| 20 | GGGUAAAGCCUCCAGAUUU |
| 21 | CAAACAGUGUGAAGGAAUU |
| 22 | GGAGAAUUGAACUGGCAAA |
| 23 | UCAUAGAGGAAGAAGAAGA |
| 24 | GCUAUUGAAUGGAGUGUGA |
| 25 | CUUAAUAGCAUGCAGAAUU |
| 26 | GAAUGAAACUGGCAAGGAU |
| 27 | AAGAUGACAUGGAGACCAA |
| 28 | UGGAAGAUGUAGAAGUAGA |
| 29 | AAGGAAUCAUAGAGGAAGA |
| 30 | AAUCUAUAGUGGAAGGAAU |
| 31 | CCAAGAAAGACCAUCCAUA |
| 32 | CAUGAUUGAUGUUGUAGAA |

TABLE 2 -continued

Further PME-1 specific siRNAs

| SEQ ID NO | siRNA sense sequence (5' to 3') |
|---|---|
| 33 | GUGGAUAGCAUCACAAGAA |
| 34 | CAUAGAGGAAGAAGAAGAA |
| 35 | GAACAAAGGUCAAGAAUCC |
| 36 | GAAUCAUAGAGGAAGAAGA |

Suitable dsRNAs include those having a greater than 80% sequence identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% sequence identity with SEQ ID NO:s 1 to 36, as long as they have similar binding properties and PME-1 silencing activity as the reference dsRNAs.

Still further PME-1 specific dsRNAs suitable for use in various embodiments of the present invention can be designed and synthetized according to methods known in the art. Any such isolated dsRNA must be sufficiently complementary to PME-1 cDNA sequence in order to silence PME-1 gene.

Artificial microRNA (miRNA) precursors are another class of small RNAs suitable for mediating RNAi. Typically, artificial miRNA precursors are about 21-25 nucleotides in length, and they may have 1 to 3, typically 2, overhanging 3' nucleotides. PME-1 silencing artificial miRNA precursors may be designed and synthetized by methods known in the art.

Short-hairpin RNAs (shRNAs) are still another way of silencing PME-1. ShRNAs consist of i) a short nucleotide sequence, typically ranging from 19 to 29 nucleotides, derived from the target gene; ii) a loop, typically ranging between 4 to 23 nucleotides; and iii) a short nucleotide sequence reversely complementary to the initial target sequence, typically ranging from 19 to 29 nucleotides. PME-1 silencing shRNAs may be designed and synthetized by means and methods known to a skilled person. Non-limiting examples of PME-1 specific shRNAs include those listed in Table 3.

TABLE 3

PME-1 specific shRNAs

| SEQ ID NO | shRNA sequence (5' to 3') |
|---|---|
| 37 | CTGGTGTTGATAGATTGGATA |
| 38 | CCCAGGTTAAATACAGCCCAT |
| 39 | GCTTATCCAATCTCTTTCTTA |

PME-1 silencing may also be obtained by antisense therapy, where relatively short (typically 13-25 nucleotides) synthetic single-stranded DNA or RNA oligonucleotides inactivate PME-1 gene by binding to a corresponding mRNA. Antisense oligonucleotides may be unmodified or chemically modified. In some embodiments, the hydrogen at the 2'-position of ribose is replaced by an O-alkyl group, such as methyl. In further embodiments, antisense oligonucleotides may contain one or more synthetic or natural nucleotide analogs including, but not limited to PNAs.

Furthermore, PME-1 silencing may obtained by ribozymes cleaving the PME-1 mRNA. The ribozyme technology is described, for example, by Li et al. in Adv. Cancer Res., 2007, 96:103-43.

As used herein, the term "PME-1 silencing" refers to complete or partial reduction of PME-1 gene expression. In some embodiments, PME-1 gene expression is reduced by at least 50%, or at least 80%, 81%, 82%, 83%, 84%, 85%, 86%, 87%, 88%, 89%, 90%, 91%, 92%, 93%, 94%, 95%, 96%, 97%, 98%, 99%, or 100% when PME-1-specific dsRNA, artificial miRNA precursor, shRNA, antisense oligonucleotide, ribozyme, or any combination thereof is introduced into a human or animal subject.

In some embodiments, PME-1 silencing may be obtained by blocking or inhibiting the interaction between PME-1 and PP2A, especially the c-subunit of PP2A, thus preventing PME-1 function towards PP2Ac at least 50%, or at least 80%, 81%, 82%, 83%, 84%, 85%, 86%, 87%, 88%, 89%, 90%, 91%, 92%, 93%, 94%, 95%, 96%, 97%, 98%, 99%, or 100%. Such blocking or inhibiting agents include, but are not limited to, recombinantly or chemically produced modified or unmodified peptides and partial peptides, as well as non-peptide molecules, such as small molecule chemical compounds. Methods for identifying such agents have been disclosed e.g. in WO 2009/100173 and US 2009/239244.

Chemical compounds suitable for use in various embodiments of the present invention include those listed in Table 4 and any stereoisomers, salts, solvates, or prodrugs thereof. In one embodiment, suitable compounds have a general formula (I):

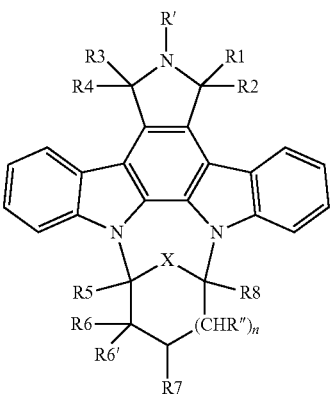

wherein
R' is H or alkyl;
R" is H or alkoxy;
R1 and R2 are H or together form oxo;
R3 and R4 are independently H or OH, or together form oxo:
R5, R6, R6', R7, and R8 are independently selected from the group consisting of H, alkyl, alkoxy, hydroxy, hydroxylalkyl, alkoxycarbonyl, monoalkylamino- and dialkylamino;
X is $CH_2$ or O; and
n is 0 or 1.

As used herein, the phrase "having the formula" is not intended to be limiting and is used the same way as the term "comprising" is commonly used.

The term "alkyl" referred to above include both linear and branched $C_{1-6}$ alkyl groups, such as methyl, ethyl, propyl, butyl, pentyl, hexyl, and the like. In some embodiments, the alkyl group is a $C_{1-3}$ alkyl group containing 1 to 3 carbon atoms.

As used herein, the term "alkoxy" refers to both linear and branched $C_{1-6}$ alkoxy groups, such as methoxy, ethoxy, propoxy, and the like. In some embodiments, the alkoxy group is a $C_{1-3}$ alkoxy group containing 1 to 3 carbon atoms.

As used herein, the term "hydroxyalkyl" refers to any of the above-mentioned $C_{1-6}$ alkyl groups substituted by —OH.

As used herein, the term "alkoxycarbonyl" refers to any of the above-mentioned $C_{1-6}$ alkoxy groups substituted by —COOH.

The term "amino" refers to —$NH_2$.

The term "monoalkylamino" includes any of the above-mentioned alkyl groups substituted with an amino group.

The term "dialkylamino" refers to any of the above-mentioned alkyl groups substituted with two amino groups.

As used herein, the term "stereoisomer" is a general term for all isomers of individual molecules that differ only in the orientation of their atoms in space. It includes enantiomers and isomers of compounds with more than one chiral center that are not mirror images of one another (diastereomers).

As used herein, the term "chiral center" or "asymmetric center" refers to a carbon atom to which four different groups are attached.

The term "enantiomer" refers to a molecule that is non-superimposeable on its mirror image and hence optically active, wherein the enantiomer rotates the plane of polarized light in one direction and its mirror image rotates the plane of polarized light in the opposite direction.

The term "racemic" refers to a mixture of equal parts of enantiomers and which is optically inactive.

Any of the disclosed compounds may be converted to a pharmaceutically acceptable salt. The pharmaceutically acceptable salt is not particularly limited as long as it is non-toxic. Non-limiting examples of salts with an inorganic or organic base include alkali metal salts (e.g. sodium salt, potassium salt and the like), alkaline earth metal salts (e.g. calcium salt, magnesium salt and the like), ammonium salts, amine salts (e.g. triethylamine salt), and the like. Non-limiting examples of acid addition salts derived from mineral acid (e.g. hydrochloride acid, hydrobromic acid, hydroiodic acid, phosphoric acid, nitric acid, sulphuric acid and the like), and salts derived from organic acids (e.g. tartaric acid, acetic acid, citric acid, malic acid, lactic acid, fumaric acid, maleic acid, benzoic acid, glycol acid, gluconic acid, succinic acid and the like).

Any of the disclosed compounds may be used as a prodrug for the below-mentioned pharmaceutical composition. As used herein, the term "prodrug" refers to any compound that can be converted to an active drug in vivo after administration, e.g. by being metabolized.

Non-limiting examples of compounds having Formula (I) include staurosporine (STS), PKC412, K252a, UCN-01, CEP-701, and SB-218078 listed in Table 4.

TABLE 4

Examples of staurosporine analogues/derivatives tested. The amount of apoptotic nuclear fragmentation (Potentiation %) in T98G glioblastoma cells after transfection with PME-1 specific dsRNA and treatment with an indicated concentration of different staurosporine analogues/derivatives are shown.

| Drug (Synonyms) | Chemical Name | CAS number | Concentration | Potentiation % (Scale) | Structure |
|---|---|---|---|---|---|
| Staurosporine | [9S-(9α,10β,11β,13α)]-2,3,10,11,12,13-Hexahydro-10-methoxy-9-methyl-11-(methylamino)-9,13-epoxy-1H,9H-diindolo[1,2,3-gh:3',2',1'-lm]pyrrolo[3,4-j][1,7]benzodiazonin-1-one | 62996-74-1 | 50 nM | 50-60% (++) | 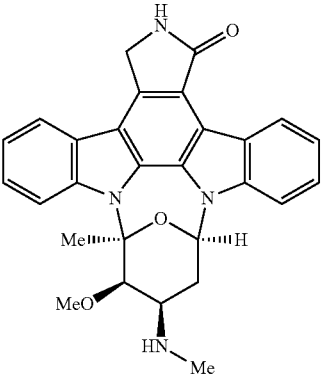 [SMILES: CN[C@@H]1C[C@H]2O[C@@](C)([C@@H]1OC)n1c3ccccc3c3c4c(c5c6ccccc6n2c5c31)C(=O)NC4] |
| PKC412/ Midostaurin/ 4'-N-benzoyl staurosporine/ CGP 41251 | [9S-(9α,10β,11β,13α)]-N-(2,3,10,11,12,13-Hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)-N-methyl benzamide | 120685-11-2 | 500 nM<br>5 μM | 5-10% (−)<br>75-80% (+++) | 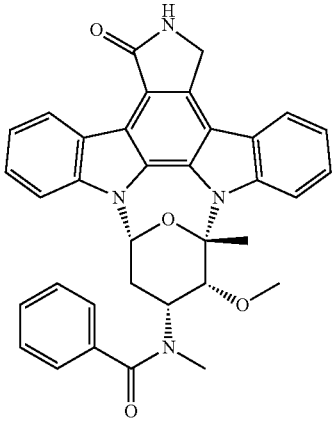 [SMILES: CO[C@@H]1[C@H](N(C)C(=O)c2ccccc2)C[C@H]2O[C@]1(C)n1c3ccccc3c3c4c(c5c6ccccc6n2c5c31)C(=O)NC4] |
| K252a/ SF 2370 | (9S,10R,12R)-2,3,9,10,11,12-Hexahydro-10-hydroxy-9-methyl-1-oxo-9,12-epoxy-1H-diindolo[1,2,3-fg:3',2',1'kl]pyrrolo[3,4-i][1,6]benzodiazocine-10-carboxylic acid methyl ester | 99533-80-9 | 500 nM<br>5 μM | 10-15% (−)<br>80-90% (++++) | 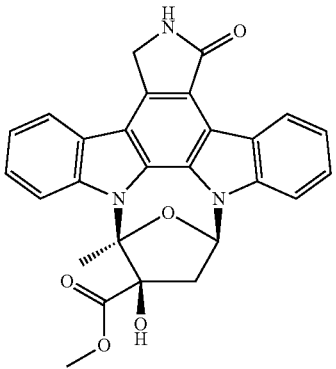 [SMILES: COC(=O)[C@@]1(O)C[C@H]2O[C@]1(C)n1c3ccccc3c3c4c(c5c6ccccc6n2c5c31)C(=O)NC4] |

TABLE 4-continued

Examples of staurosporine analogues/derivatives tested. The amount of apoptotic nuclear fragmentation (Potentiation %) in T98G glioblastoma cells after transfection with PME-1 specific dsRNA and treatment with an indicated concentration of different staurosporine analogues/derivatives are shown.

| Drug (Synonyms) | Chemical Name | CAS number | Concentration | Potentiation % (Scale) | Structure |
| --- | --- | --- | --- | --- | --- |
| UCN-01/ 7-Hydroxy-staurosporine | (9S)-2,3,10,11,12,13-Hexahydro-3α-hydroxy-10α-methoxy-9-methyl-11α-methyl amino-9β,13β-epoxy-1H,9H-diindolo[1,2,3-gh:3',2',1'-lm]pyrrolo[3,4-j][1,7]benzodiazonin-1-one | 112953-11-4 | 50 nM 5 μM | 5-10% (−) 80-90% (++++) | 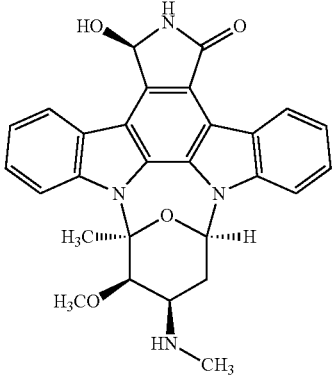 [SMILES: CN[C@@H]1C[C@H]2O[C@@](C)([C@@H]1OC)n1c3ccccc3c3c4c(c5c6ccccc6n2c5c31)C(=O)N[C@@H]4O] |
| CEP-701/ Lestaurtinib | (9S,10S,12R)-2,3,9,10,11,12-Hexahydro-10-hydroxy-10-(hydroxymethyl)-9-methyl-9,12-epoxy-1H-diindolo[1,2,3-fg:3',2',1'-kl]pyrrolo[3,4-i][1,6]benzodiazocin-1-one | 111358-88-4 | 50 nM 5 μM | 2-5% (−) 75-80% (+++) | 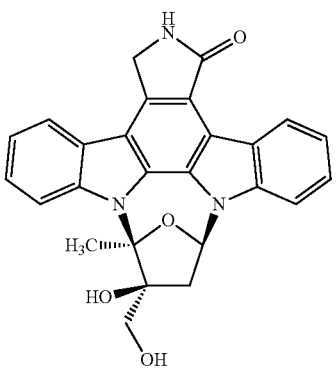 [SMILES: C[C@]12O[C@H](C[C@]1(O)CO)n1c3ccccc3c3c4c(c5c6ccccc6n2c5c31)CNC4=O] |
| SB-218078 | 9,10,11,12-Tetrahydro-9,12-epoxy-1H-diindolo[1,2,3-fg:3',2',1'-kl]pyrrolo[3,4-i][1,6]benzodiazocine-1,3(2H)-dione | 135897-06-2 | 50 nM 5 μM | 2-5% (−) 25-30% (+) | 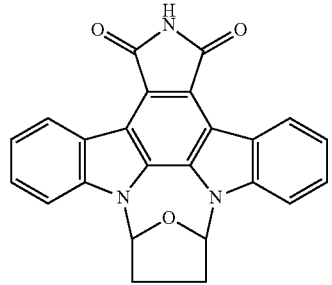 [SMILES: O=C1NC(=O)c2c1c1c3ccccc3n3c1c1c2c2ccccc2n1C1CCC3O1] |
| GÖ-6976 | 12-(2-Cyanoethyl)-6,7,12,13-tetrahydro-13-methyl-5-oxo-5H-indolo[2,3-a]pyrrolo[3,4-c]carbazole | 136194-77-9 | 5 μM | 15-20% (−) | 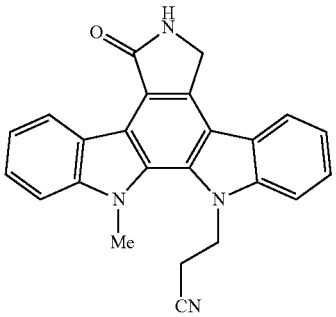 [SMILES: Cn1c2ccccc2c2c3c(c4c5ccccc5n(CCC#N)c4c21)CNC3=O] |

TABLE 4-continued

Examples of staurosporine analogues/derivatives tested. The amount of apoptotic nuclear fragmentation (Potentiation %) in T98G glioblastoma cells after transfection with PME-1 specific dsRNA and treatment with an indicated concentration of different staurosporine analogues/derivatives are shown.

| Drug (Synonyms) | Chemical Name | CAS number | Concentration | Potentiation % (Scale) | Structure |
|---|---|---|---|---|---|
| K252c/ Staurosporine aglycone/ Staurosporinone | 6,7,12,13-Tetrahydro-5H-indolo[2,3-a]pyrrolo[3,4-c]carbazol-5-one | 85753-43-1 | 5 µM | 15-20% (−) | 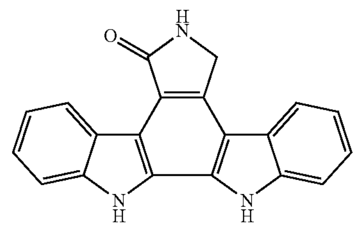 [SMILES: O=C1NCc2c1c1c3ccccc3[nH]c1c1[nH]c3ccccc3c21] |
| Enzastaurin/ LY-317615 | 3-(1-Methyl-1H-indol-3-yl)-4-(1-(1-(2-pyridinyl methyl)-4-piperidinyl)-1H-indol-3-yl)-1H-pyrrole-2,5-dione | 170364-57-5 | 5 µM | 15-20% (−) | 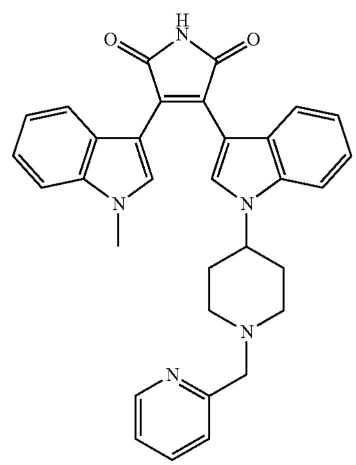 [SMILES: Cn1cc(C2=C(c3cn(C4CCN(Cc5ccccn5)CC4)c4ccccc34)C(=O)NC2=O)c2ccccc21] |
| RO-31-8220/ Bisindolyl maleimide IX, Methane sulfonate | 3-[1-[3-(Amidinothio) propyl-1H-indol-3-yl]-3-(1-methyl-1H-indol-3-yl)maleimide | 138489-18-6 | 5 µM | 5-10% (−) | 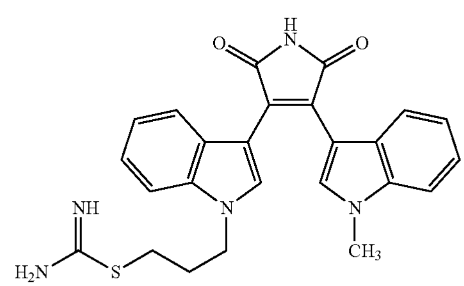 [SMILES: Cn1cc(C2=C(c3cn(CCCSC(=N)N)c4ccccc34)C(=O)NC2=O)c2ccccc21] |
| Arcyriaflavin A | 12,13-Dihydro-5H-indolo[2,3-a]pyrrolo[3,4-c]carbazole-5,7(6H)-dione | 118458-54-1 | 5 µM | 5-10% (−) | 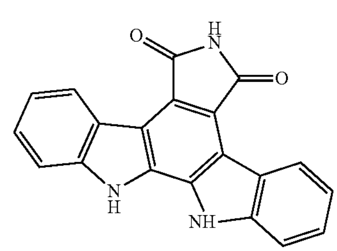 [SMILES: O=C1NC(=O)c2c1c1c3ccccc3[nH]c1c1[nH]c3ccccc3c21] |

TABLE 4-continued

Examples of staurosporine analogues/derivatives tested. The amount of apoptotic nuclear fragmentation (Potentiation %) in T98G glioblastoma cells after transfection with PME-1 specific dsRNA and treatment with an indicated concentration of different staurosporine analogues/derivatives are shown.

| Drug (Synonyms) | Chemical Name | CAS number | Concentration | Potentiation % (Scale) | Structure |
|---|---|---|---|---|---|
| Rebeccamycin | 5h-indolo(2,3-a)pyrrolo(3,4-c)carbazole-5,7(6h)-dione,1,11-dichloro-12,13-dihy;dro-12-(4-o-methyl-beta-d-glucopyranosyl) | 93908-02-2 | 5 µM | 5-10% (−) | 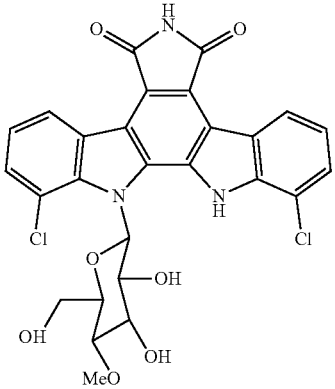 [SMILES: COC1C(CO)OC(n2c3c(Cl)cccc3c3c4c(c5c6cccc(Cl)c6[nH]c5c32)C(=O)NC4=O)C(O)C1O] |

Administration of PME-1 dsRNAs and compounds of formula (I) may be concomitant, simultaneous, or subsequent.

Delivery of PME-1 specific dsRNAs can be accomplished in two principally different ways: 1) endogenous transcription of a nucleic acid sequence encoding the oligonucleotide, where the nucleic acid sequence is located in an expression construct or 2) exogenous delivery of the oligonucleotide.

For endogenous transcription, PME-1 specific dsRNAs may be inserted into suitable expression systems using methods known in the art. Non-limiting examples of such expression systems include retroviral vectors, adenoviral vectors, lentiviral vectors, other viral vectors, expression cassettes, and plasmids, such as those encapsulated in pegylated immunoliposomes (PILs), with or without one or more inducible promoters known in the art. Both dsRNA strands may be expressed in a single expression construct from the same or separate promoters, or the strands may be expressed in separate expression constructs.

The above-mentioned expression systems may also be used for the delivery of PME-1 silencing artificial miRNA precursors and shRNAs.

Typically, expression constructs are formulated into pharmaceutical compositions prior to administration to a human or animal subject (e.g. a canine subject). Administration may be performed by any suitable method known in the art, including systemic and local delivery. The formulation depends on the intended route of administration as known to a person skilled in the art. By way of example, the expression construct may be delivered in a pharmaceutically acceptable carrier or diluent, or it may be embedded in a suitable slow release composition. In some cases, the pharmaceutical composition may contain one or more cells producing the expression construct. Also bacteria may be used for RNAi delivery. For instance, recombinantly engineered Escherichia coli can enter mammalian cells after in vivo delivery and transfer shRNAs. A related approach is to use minicells derived e.g. from Salmonella enterica.

For exogenous delivery, dsRNA molecules are typically complexed with liposome or lipid-based carriers, cholesterol conjugates, or polyethyleneimine (PEI). A promising new approach is to complex dsRNAs with stable nucleic acid lipid particles (SNALPs). Suitable routes of administration for exogenous delivery, with or without said complexing, include, but are not limited to, parenteral delivery (e.g. intravenous injection), enteral delivery (e.g. orally), local administration, topical administration (e.g. dermally or transdermally) as known to a person skilled in the art. Since surgical removal of a tumour is usually the primary clinical intervention, dsRNAs may be administered directly to the resected tumour cavity.

Chemotherapeutic agents of formula (I) may be administered to a human or animal subject by any suitable route known in the art including, but not limited to, those listed for the administration of PME-1 specific dsRNAs.

In the present combination therapy, dsRNA molecules and compounds of formula (I) may be formulated into the same or separate pharmaceutical composition. When separate pharmaceutical compositions are used, administration may be concomitant, simultaneous, or subsequent. The formulation and/or route of administration for dsRNA molecules and compounds of formula (I) may be selected independently from each other. In some embodiments, the pharmaceutical composition may comprise one or more different PME-1 silencing dsRNAs and/or one or more chemotherapeutic agents of formula (I).

The pharmaceutical compositions may be administered in any appropriate pharmacological carrier suitable for administration. They can be administered in any form that effect prophylactic, palliative, preventive or curing hyperproliferative diseases, such as cancer, in human or animal patients.

For the purposes of parenteral or topical administration, dsRNAs and/or compounds of formula (I) may be formulated, for instance, as solutions, suspensions or emulsions. The formulations may comprise aqueous or non-aqueous solvents, co-solvents, solubilizers, dispersing or wetting agents, suspending agents and/or viscosity agents, as needed. Non-limiting examples of non-aqueous solvents are propylene glycol, polyethylene glycol, vegetable oil, fish oil, and injectable organic esters. Aqueous carriers include, for instance, water, water-alcohol solutions, including saline and buffered medial parenteral vehicles including sodium chloride solution, Ringer's dextrose solution, dextrose plus sodium chloride solution, Ringer's solution containing lactose, or fixed oils. Non-limiting examples of intravenous vehicles include fluid and nutrient replenishers, electrolyte replenishers, such as those based on Ringer's dextrose and the like. Aqueous compositions may comprise suitable buffer agents, such as sodium and potassium phosphates, citrate, acetate, carbonate or glycine buffers depending on the targeted pH-range. The use of sodium chloride as a tonicity adjuster is also useful. The compositions may also include other excipients, such as stabilizing agents or preservatives. Useful stabilizing excipients include surfactants (polysorbate 20 & 80, poloxamer 407), polymers (polyethylene glycols, povidones), carbohydrates (sucrose, mannitol, glucose, lactose), alcohols (sorbitol, glycerol propylene glycol, ethylene glycol), suitable proteins (albumin), suitable amino acids (glycine, glutamic acid), fatty acids (ethanolamine), antioxidants (ascorbic acid, cysteine etc.), chelating agents (EDTA salts, histidine, aspartic acid) or metal ions (Ca, Ni, Mg, Mn). Among useful preservative agents are benzyl alcohol, chlorbutanol, benzalkonium chloride and possibly parabens.

Solid dosage forms for oral administration include, but are not limited to, capsules, tablets, pills, troches, lozenges, powders and granules. In such solid dosage forms, dsRNAs and/or compounds of formula (I) may be admixed with at least one inert diluent such as sucrose, lactose or starch. Such dosage forms may also comprise, as is normal practice, pharmaceutical adjuvant substances, e.g. stearate lubricating agents or flavouring agents. Solid oral preparations can also be prepared with enteric or other coatings which modulate release of the active ingredients.

Non-limiting examples of liquid dosage forms for oral administration include pharmaceutically acceptable emulsions, solutions, suspensions, syrups and elixirs containing inert non-toxic diluents commonly used in the art, such as water and alcohol. Such compositions may also comprise adjuvants, such as wetting agents, buffers, emulsifying, suspending, sweetening and flavouring agents.

The pharmaceutical composition may be provided in a concentrated form or in a form of a powder to be reconstituted on demand. In case of lyophilizing, certain cryoprotectants are preferred, including polymers (povidones, polyethylene glycol, dextran), sugars (sucrose, glucose, lactose), amino acids (glycine, arginine, glutamic acid) and albumin. If solution for reconstitution is added to the packaging, it may consist e.g., of sterile water for injection or sodium chloride solution or dextrose or glucose solutions.

Means and methods for formulating the present pharmaceutical preparations are known to persons skilled in the art, and may be manufactured in a manner which is in itself known, for example, by means of conventional mixing, granulating, dissolving, lyophilizing or similar processes.

The present combination therapy may be used to treat human or animal hyperproliferative diseases including, but not limited to psoriasis, myocardial hypertrophy, benign tumors such as adenoma, hamartoma and chondroma, as well as cancers such as squamous cell carcinomas of the head and neck, colon cancer, gastric cancer, breast cancer, ovarian cancer, prostate cancer, cervical cancer, brain cancers (e.g. gliomas, astrocytomas, and glioblastomas), and haematological cancers (e.g. chronic and acute myeloid leukaemia).

As used herein, the term "treatment" or "treating" refers not only to complete cure of a disease, but also to prevention, alleviation, and amelioration of a disease or symptoms related thereto.

By an "efficient amount" of a combination of dsRNAs and compounds of formula (I) is meant an amount in which the harmful effects of a tumor are, at a minimum, ameliorated. Amounts and regimens for the administration of the present combination therapy can be determined readily by those with ordinary skill in the clinical art of treating cancer-related disorders. Generally, the dosage of the present combination therapy depend on considerations such as: age, gender and general health of the patient to be treated; kind of concurrent treatment, if any; frequency of treatment and nature of the effect desired; extent of tissue damage; duration of the symptoms; and other variables to be adjusted by the individual physician. A desired dose can be administered in one or more applications to obtain the desired results. Pharmaceutical compositions according to the present embodiments may be provided in unit dosage forms.

In one embodiment, dsRNAs may be administered in an effective amount within the dosage range of about 0.01 µg/kg to about 10 mg/kg, or about 1.0 µg/kg to about 10 µg/kg. DsRNAs may be administered in a single daily dose, or the total daily dosage may be administered in divided doses, e.g. of two, three or four times daily.

In one embodiment, compounds of formula (I) may be administered in an effective amount within the dosage range of about 0.1 µg/kg to about 300 mg/kg, or about 1.0 µg/kg to about 10 mg/kg. The compounds of formula (I) may be administered in a single daily dose, or the total daily dosage may be administered in divided doses, e.g. of two, three or four times daily. The dosing schedule may be selected independently from the dosing schedule of dsRNAs.

It will be obvious to a person skilled in the art that, as the technology advances, the inventive concept can be implemented in various ways. The invention and its embodiments are not limited to the examples described below but may vary within the scope of the claims.

Examples

Materials and Methods

Eukaryotic Cell Culture and Small Interfering RNA (siRNA) Transfections:

For this study, we used T98G, U118MG, U251MG and U87MG human glioblastoma cell lines. T98G and U251MG cells were cultured in Eagle's MEM, U118MG in DMEM (Sigma-Aldrich) and U87MG in DMEM/F-12 (Gibco Products, Invitrogen) media supplemented with 10% heat-inactivated FCS and penicillin (100 units/mL)-streptomycin (100 Ag/mL) in a humidified atmosphere of 5% CO2 at 37° C. Small interfering RNA (siRNA) transfections were performed with Lipofectamine RNAiMAX reagent (Invitrogen) according to the manufacturer's instructions. Transfections were performed using forward transfection protocol in all the experiments except for CellTiter-glo and Caspase-glo assay, where reverse transfections were performed in 96-well plates. Following siRNA sequences were used: scrambled (5'-GUA ACA AUG AGA GCA CGG C-3'; SEQ ID NO:40), PME-1 (5'-GGA AGU GAG UCU AUA AGC A-3'; SEQ ID NO:1), PME-1 (5'-UCA UAG AGG AAG AAG AAG A-3'; SEQ ID NO:2) or PME-1 (5'-AGG UCA AGA AUC CUG AAG A-3'; SEQ ID NO:3), CIP2A (5'-CUG UGG UUG UGU UUG CAC U-3'; SEQ ID NO:41), PPP2R2A (5'-CUG CAG AUG AUU UGC GGA U-3'; SEQ ID NO:42), PPP2R2C (5'-ACC GCU CAU UCU UCU CGG AAA-3'; SEQ ID NO:43), PPP2R3B (5'-CAC GUG UCU CUG UCA CGU G-3'; SEQ ID NO:44), PPP2R5A (5'-CUG UAU CAU GGC CAU AGU A-3'; SEQ ID NO:45) and PPP2R5B (5'-CCG CAU GAU CUC AGU GAA U-3'; SEQ ID NO:46).

Chemical Inhibitors and Drugs:

A small inhibitor screening set containing H-7, H-8, H-89, Chelerythrine chloride (Chl Cl), Sunitinib, Tandutinib, Lapatinib, Vandetanib, PKC412 and K252a was purchased from Biaffin GmbH & Co KG. Topotecan Hydrochloride was purchased from Selleck Chemicals. UO126, LY 294002, RO-31-8220, GÖ 6976 and SB 218078 were purchased from Calbiochem. Staurosporine (STS), CEP-701, UCN-01 were obtained from Sigma-Aldrich; Temozolomide (TMZ), Arcyriaflavin-A and K252c from Tocris Bioscience; Rebeccamycin from Enzo Life Sciences and Enzastaurin from LC laboratories. Pan-caspase inhibitor Z-VAD-FMK, PP2A inhibitor Okadaic acid, and activators Sodium selenate and Xylulose-5-phosphate were obtained from Sigma-Aldrich. Another PP2A activator FTY720 was purchased from Cayman chemicals. Human recombinant Fc-FasL fusion protein and human recombinant isoleucine-zipper TRAIL (TRAIL) were a gift from Professor. John Eriksson (Abo Akademi University). All the chemicals were reconstituted as recommended by the supplier in either water or DMSO.

Western Blotting and Antibodies:

Cultured and treated cells were lysed in 2×SDS sample buffer/Laemmli Buffer, boiled and resolved by SDS-PAGE using 10% acrylamide gels. Proteins were transferred to PVDF membranes. Membranes were blocked and incubated with required dilution of primary and 1:5000 dilution of secondary antibody in 5% Milk-PBS-Tween20 for required duration of time and developed by enhanced chemiluminescence (ECL). Anti-PME-1 (clone H-226) and anti-CIP2A (clone 2G10-3B5) antibodies (1:1000 dilution) were purchased from Santa Cruz Biotechnology. Anti-actin (clone AC-40) antibody (1:10,000 dilution) was purchased from Sigma-Aldrich. Densitometric analysis of western blots was performed using MCID image analyzer software.

Cell Viability Assay:

Cell viability was determined by CellTiter-glo (CTG) assay which measures the cellular ATP levels as an indicator of metabolically active and viable cells. CTG reagent kit was purchased from Promega Corp. and assays were performed according to their recommendations. Assays were performed in white polystyrene 96-well plates (Nunc, Thermo Fisher Scientific Inc.) and luminescence was measured with Perkin Elmer Victor2 Plate Reader.

Analysis of Caspase-3 and -7 Activity:

Caspase-3 and -7 activity was measured by luminescence based method, which utilize a substrate containing Caspase-3 and -7 target peptide DEVD, named Caspase-Glo 3/7 Assay (Promega Corp.). Assays were performed in white polystyrene 96-well plates (Nunc, Thermo Fisher Scientific Inc.) according to manufacturer's instructions and luminescence was measured with Perkin Elmer Victor2 Plate Reader.

Apoptosis Assay by Sub-G0/G1 Fraction Estimation:

The percentage of the sub-G0/G1 fraction containing fragmented nuclei stained with Propidium iodide (PI) was taken as a measure of apoptotic cells. $3.5\text{-}4\times 10^4$ cells were plated in 24-well plates, transfected with siRNA for 48 hrs, and then treated with indicated concentration of test compounds in fresh media. After 24 hrs of treatment, both floating and adherent cells were harvested by centrifugation. Cell pellets were resuspended in 400 μl of hypotonic PI buffer, containing 40 mM Tri-sodium citrate (Merck), 0.3% Triton X-100 (Sigma-Aldrich) and 50 μg/ml Propidium iodide (Sigma-Aldrich) in PBS, and incubated at room temperature for 10 minutes in dark. The flow cytometric analysis of PI stained nuclei was performed and the recorded data was analyzed using a FACScan flow cytometer and software (Becton Dickinson) respectively.

In experiments using pan-caspase inhibitor, cells were kept in growth media containing 30 μM Z-VAD-FMK starting from 18 hrs after transfection till the PI staining. For treatment with PP2A activators FTY720, Sodium Selenate and Xylulose-5-phosphate, cells were kept in respective drugs throughout the experiment starting from 24 hrs after transfection. PP2A inhibitor, Okadaic acid, treatment was given for 24 hrs after 24 hrs of transfection.

Colony Formation Assay:

Cells plated in very low density ($4\text{-}6\times 10^3$) in 6-well plates were allowed to grow for about 7 days until they form small colonies. These cells were then transfected with Scrambled or PME-1 siRNA using Lipofectamine RNAiMAX reagent (Invitrogen) according to the manufacturer's instructions. After 48 hrs, treatments were given with indicated concentration of chemical drugs for another 48 hrs. Cell colonies were washed with PBS, fixed with 3.7% formaldehyde and stained with 0.2% crystal violet solution (made in 10% ethanol) for 15 minutes at room temperature each. Excess stain was removed by repeated washings with PBS. Plates were dried and pictures were taken with Olympus SP-600UZ camera or Epson perfection V700 scanner and analysed with ImageJ.

Statistical Analysis:

The significance level of differences between the mean values of two groups of data was evaluated using the unpaired Student's t-test assuming equal variances among the sample means. All p-values were two-tailed. Parameters with probability value $p<0.05$ was depicted as statistically significant and $p<0.001$ as highly significant difference.

Results

In order to study the effect of PME-1 inhibition on cancer cell survival and sensitivity to different chemical drugs, at first, human glioblastoma T98G cells were transiently transfected with PME-1 siRNA for 72 hs to effectively reduce PME-1 protein levels (FIG. 1A). The T98G cells containing normal or reduced levels of PME-1 (cells transfected with Scrambled siRNA depicted in SEQ ID NO:37 or PME-1 siRNA depicted in SEQ ID NO:1, respectively) were treated with different chemical drugs including broadly specific inhibitors of serine-threonine protein kinases (H7, H8, H89, Chelerythrine chloride, UO126, LY 294002 and Staurosporine), inhibitors of tyrosine kinases (Sunitinib, Tandutinib, Lapatinib and Vandetanib), DNA topoisomerase I inhibitor (Topotecan) and a DNA methylating drug, Temozolomide, which is currently used for the treatment of glioblastoma multiforme (GBM).

Figure 1B:
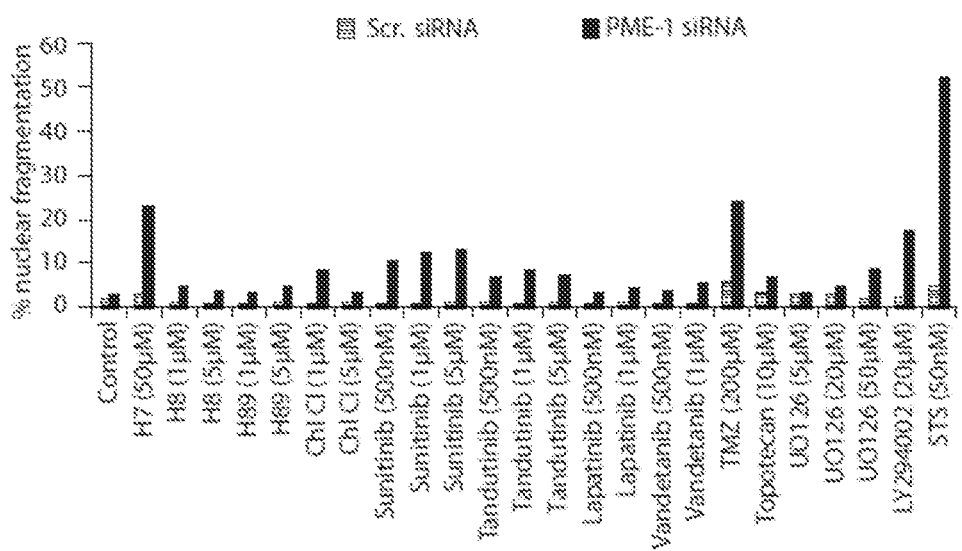
FIG. 1B displays the amount of apoptotic nuclear fragmentation in T98G glioblastoma cells induced by transfection of either scrambled or PME-1 specific dsRNA for 48 hours, and then treatment with indicated concentration of different drugs/chemical inhibitors for another 24 hours. Abbreviations: Chl Cl—chelerythrine chloride, TMZ—temozolomide, STS—staurosporine.
Figure 1C:
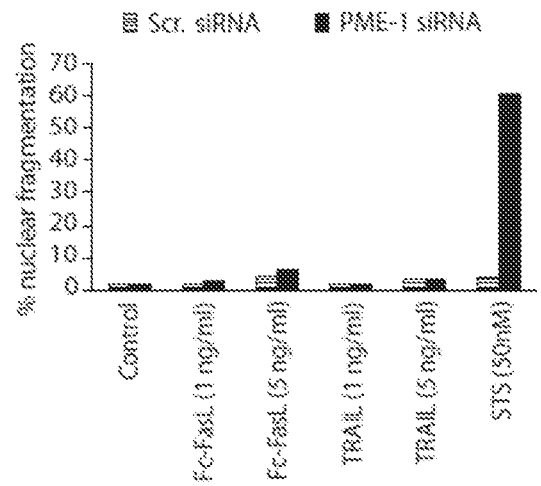
FIG. 1C shows the amount of apoptotic nuclear fragmentation in T98G glioblastoma cells induced by transfection of either scrambled or PME-1 specific dsRNA for 48 hours, and then treatment with indicated concentration of staurosporine (STS) or cell death inducing ligands, recombinant FasL and TRAIL, for another 24 hours.

The T98G cells transfected with siRNA for 48 hrs were given drug treatments for 24 hrs and were subsequently lysed, and their nuclei were stained using hypotonic propidium iodide buffer. The lysates were analysed for changes in the sub-G0/G1 fraction of fragmented nuclei by flow cytometry (FACS) (FIG. 1B). Condensation and fragmentation of nucleus is a key biochemical feature of apoptosis and sub-G0/G1 analysis has been widely used for detection of apoptosis (FEBS Lett., 1986, 194(2):347-50; Cytometry, 1991, 12(4):323-329; Nature Protocols, 2006, 1:1458-1461). Using this technique, H7, Sunitinib and LY 294002 showed moderate levels of apoptosis in PME-1 depleted cells. The chemotherapeutic drug Temozolomide also induced cell death in glioblastoma cells to moderate levels, but did not benefit much when used in combination with PME-1 siRNA. The most outstanding candidate of all tested drugs was Staurosporine (STS) which induced very high level of apoptosis in PME-1 depleted glioblastoma T98G cells with STS concentration that did not alone induce significant nuclear fragmentation. The synergistic effect of PME-1 depletion was found to be specific to STS because treatment of cells with most of the chemical compounds (FIG. 1B) or with cell death inducing ligands, FasL (recombinant Fc-FasL fusion protein) and TRAIL (FIG. 1C) did not show the same trend.

Figure 1D:
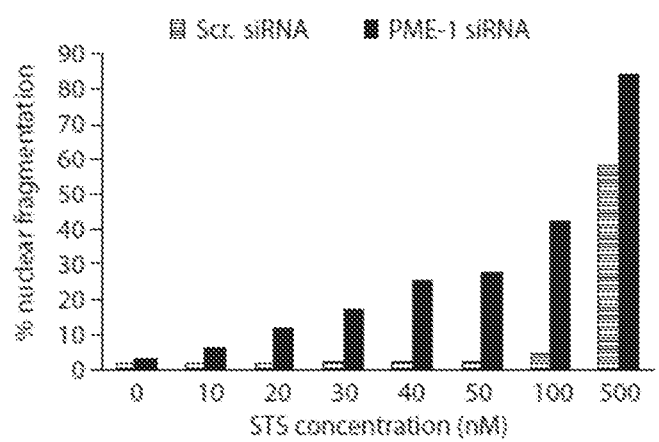
FIG. 1D shows the dose dependent increase in the apoptosis of PME-1 dsRNA transfected T98G cells with increasing concentration of staurosporine, as compared to scrambled dsRNA transfected cells.

Moreover, STS was found to induce apoptosis in a dose dependent manner in PME-1 depleted cells at concentrations that did not induce cell death in scrambled siRNA transfected cells (FIG. 1D). However, at concentrations higher than 50 nM, STS alone started inducing cell death even in control (Scrambled siRNA transfected) T98G cells.

Figure 1E:
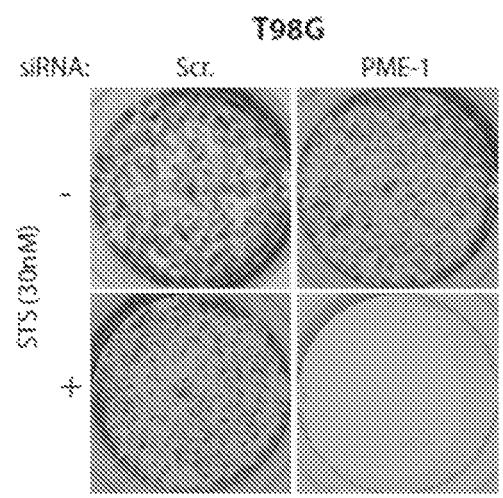
FIGS. 1E and 1F represent the colonogenic potential of T98G and U118MG glioblastoma cells respectively, after transfection of scrambled or PME-1 dsRNA and treatment with indicated concentration of staurosporine for 2 days.
Figure 1F:
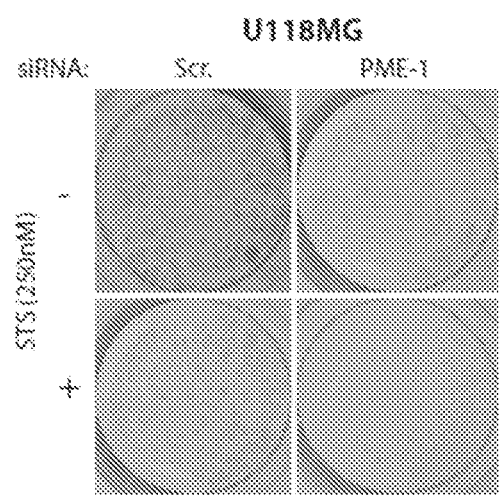

The efficacy of this treatment combination was then tested by colony formation assay in T98G glioblastoma cells and another glioblastoma cell line U118MG. For this experiment, these cells were grown in 6-well plates until the formation of small colonies which were then transfected with Scrambled or PME-1 siRNA for 48 hrs followed by treatment with STS at the indicated concentrations for another 48 hrs. Colonies were fixed with formaldehyde, stained with crystal violet and pictures were analysed with Image J. In both the cell lines, either PME-1 depletion or STS treatment alone moderately reduced the colony formation ability, whereas combination of these two treatments resulted in almost complete loss of colonies (FIGS. 1E and 1F).

Figure 2A:
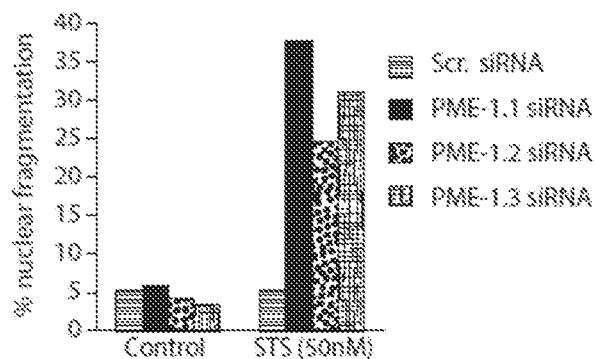
FIG. 2A represents the induction of apoptotic nuclear fragmentation by three different PME-1 dsRNAs, PME-1.1 (SEQ ID NO:1), PME-1.2 (SEQ ID NO: 2) and PME-1.3 (SEQ ID NO: 3), in combination with staurosporine treatment.
Figure 2B:
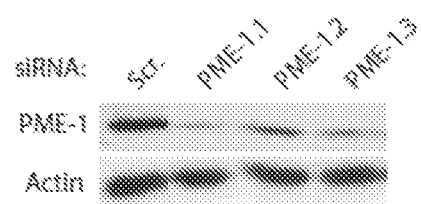
FIG. 2B a western blot demonstrating PME-1 silencing activity of a scrambled dsRNA (Scr.) and three different PME-1 specific dsRNAs (PME-1.1, i.e. SEQ ID NO: 1, PME-1.2, i.e. SEQ ID NO: 2, and PME-1.3, i.e. SEQ ID NO: 3) in T98G cells.
Figure 2C:
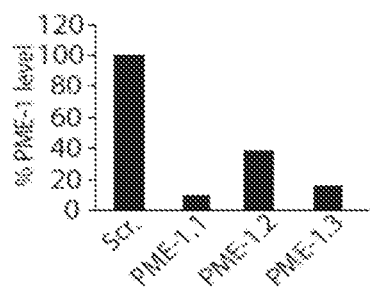
FIG. 2C is the densitometric analysis of above mentioned western blot image showing residual PME-1 levels in T98G cells transfected with PME-1 specific dsRNAs (PME-1.1, i.e. SEQ ID NO: 1, PME-1.2, i.e. SEQ ID NO: 2, and PME-1.3, i.e. SEQ ID NO: 3) as compared to scrambled siRNA transfected cells.
Figure 2D:
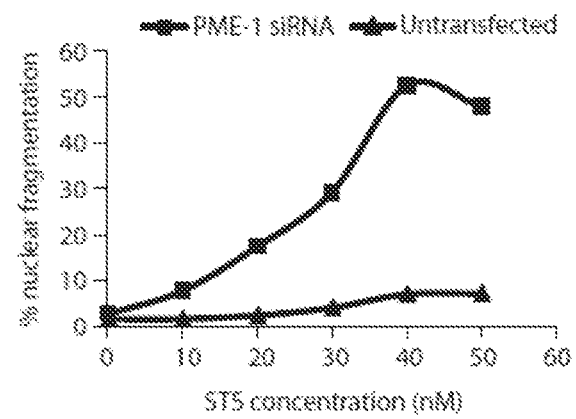
FIG. 2D shows the dose dependent increase in the apoptosis of PME-1 dsRNA transfected T98G cells with increasing concentration of staurosporine as compared to untransfected cells.

To exclude the possibility of sequence-specific off-target effect of PME-1 siRNA depicted in SEQ ID NO:1, three different PME-1 specific siRNA sequences (SEQ ID NO:s 1 to 3) were transfected to T98G cells and apoptotic nuclear fragmentation was analysed following STS treatment (FIG. 2A). Effectiveness of these PME-1 siRNAs was measured by western blotting (FIG. 2B), and band intensities were quantified and normalised with respect to beta-actin (FIG. 2C). All PME-1 siRNA sequences were capable of sensitizing glioblastoma T98G cells to STS mediated apoptosis. To eliminate any possible background effects caused by transfection of Scrambled siRNA, untransfected T98G cells were treated with increasing concentration of STS and the apoptotic nuclear fragmentation in these cells was compared with the cells receiving PME-1 siRNA and same concentration of STS (FIG. 2D). We observed limited amount of cell death with STS alone at concentrations higher than 30 nM. On the other hand, cells downregulated for PME-1 were highly sensitive to STS induced cell death even at lowest concentrations used in this experiment.

Figure 3A:
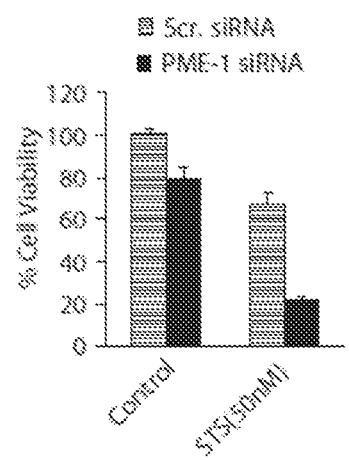
FIG. 3A shows the effect of PME-1 dsRNA transfection and staurosporine treatment on the viability of T98G cells.
Figure 3B:
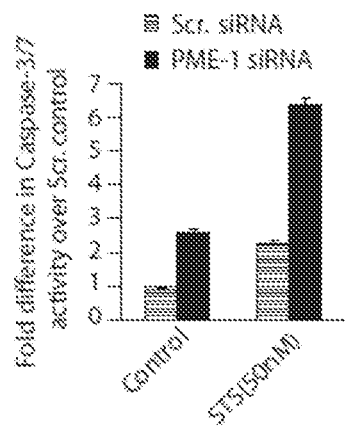
FIG. 3B shows the effect of PME-1 dsRNA transfection and staurosporine treatment on the levels of active caspase-3 and -7 in T98G cells.
Figure 3C:
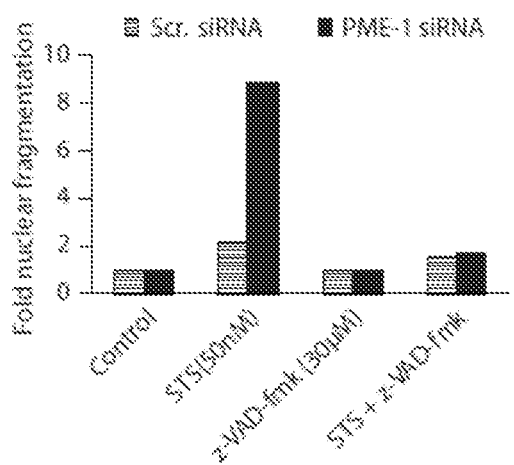
FIG. 3C shows the effect of pan-caspase inhibitor, Z-VAD-FMK treatment on PME-1 dsRNA and staurosporine mediated apoptosis, measured as the amount of nuclear fragmentation.

To study the features of cell killing induced by STS in PME-1 depleted cells we first analysed the effect of this dual combination of PME-1 siRNA and STS treatment on viability of glioblastoma T98G cells by Cell-titer-glo (CTG) assay (FIG. 3A). The results strongly correlate with the sub-G0/G1 analysis as PME-1 depletion reduces cell viability by small fraction but when the same cells also received the STS treatment there was a drastic decrease in the cell viability. Another biochemical feature of apoptosis is activation of effector cysteine-aspartic proteases Caspase-3 and 7. PME-1 depletion alone was found to increase the activity of Caspase-3/7 by more than 2 fold which in combination with STS treatment rises above 6 fold (FIG. 3B) suggesting Caspases are involved in apoptosis induction. To further verify the role of Caspase induction, cells receiving PME-1 siRNA and STS treatment were treated with pan-caspase inhibitor, z-VAD-fmk, throughout the experiment and apoptosis was analysed by nuclear fragmentation assay (FIG. 3C). We found a complete reversal of STS mediated apoptosis in PME-1 depleted cells by inhibition of Caspase activity, suggesting that this apoptosis is completely dependent on induction of Caspases.

Figure 4A:
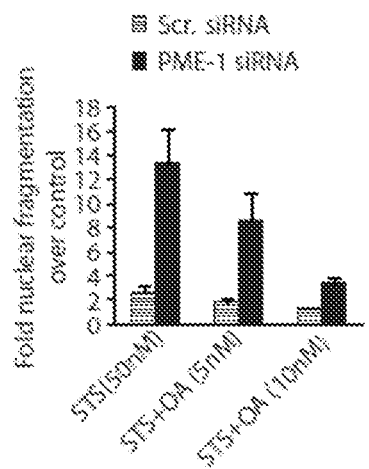
FIG. 4A shows the effect of pre-treatment of T98G cells with PP2A inhibitor, okadaic acid, on PME-1 dsRNA and staurosporine mediated apoptosis, measured as amount of nuclear fragmentation.
Figure 4B:
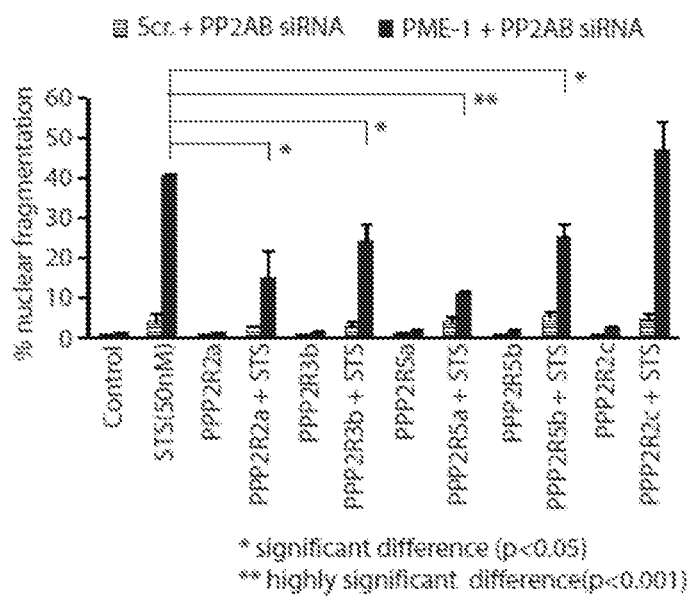
FIG. 4B represents the effect of dsRNA mediated co-depletion of different PP2A B-subunits on PME-1 specific dsRNA and staurosporine mediated apoptosis of T98G cells, measured as amount of nuclear fragmentation.

Next, our focus was to investigate the possible mechanism behind PME-1 mediated resistance of glioblastoma cells to STS induced apoptosis. Since the only established direct target of PME-1 is PP2A, we used a chemical inhibitor of PP2A, okadaic acid (OA) speculating that it should reverse the effect of PME-1 inhibition and hence promote the cell survival. Indeed, pre-treatment of glioblastoma T98G cells to OA for 24 hrs prior STS treatment was sufficient to rescue cells from PME-1 siRNA and STS mediated apoptosis in a dose dependent manner (FIG. 4A). This led us to look further into the role of PP2A and to find out which of the different PP2A trimeric complexes might be involved in PME-1 mediated apoptosis effects. Since, PME-1 promotes the binding of some and inhibit the binding of other PP2A regulatory B-subunits, we used siRNA mediated inhibition of specific B-subunits along with PME-1 inhibition to study which ones are required for PME-1 mediated effects. Nine different PP2A B-subunit siRNAs were co-transfected with PME-1 siRNA to glioblastoma T98G cells, followed by STS treatment and apoptosis analysis. As expected, only a few PP2A B-subunits when inhibited could reverse the apoptosis in PME-1 depleted cells. Representative FIG. 4B shows that the cells co-depleted for either PPP2R2a, PPP2R3b, PPP2R5a, or PPP2R5b B-subunit are capable of significantly reversing the STS mediated apoptosis in PME-1 depleted cells. Whereas, simultaneous depletion of either PPP2R2c (FIG. 4B) or other tested B-subunits (data not shown) could not affect the apoptosis of cells receiving PME-1 siRNA and STS treatment. Therefore, we can conclude that PME-1 inhibition promotes STS-mediated apoptosis by reactivation of PP2A trimers containing above four B-subunits.

Figure 4C:
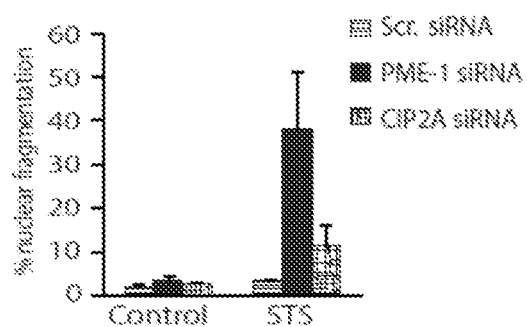
FIG. 4C shows a comparison between the apoptosis inducing potential of PME-1 specific or CIP2A specific dsRNA upon staurosporine treatment in comparison to scrambled dsRNA transfected cells.
Figure 4D:
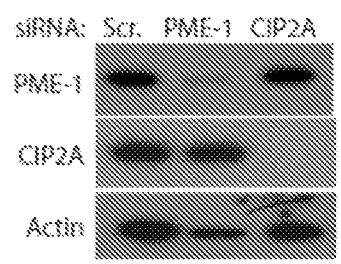
FIG. 4D is a western blot image demonstrating the PME-1 and CIP2A silencing activity of a scrambled dsRNA (Scr.), PME-1 specific dsRNA (PME-1) and CIP2A specific dsRNA (CIP2A) in human glioblastoma T98G cells.
Figure 4E:
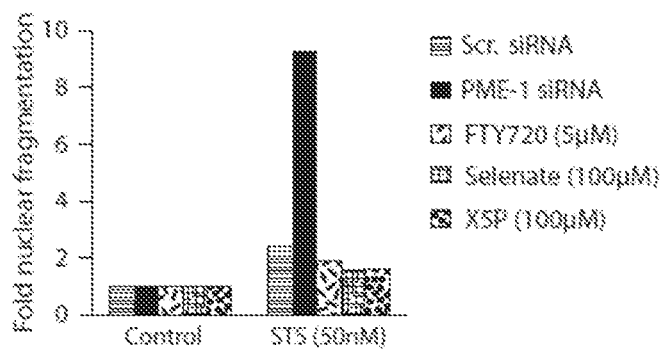
FIG. 4E shows a comparison between apoptosis mediated by staurosporine treatment in T98G cells depleted of PME-1 using specific dsRNA (PME-1) and different chemical activators of PP2A, FTY720, Selenate or Xylulose-5-phosphate (X5P).

To verify whether these PP2A-mediated apoptosis effects are specific to PME-1 or shared with other PP2A inhibitory/regulatory proteins, we compared CIP2A and PME-1 depletion for their ability to sensitize glioblastoma cells to apoptosis in response to STS treatment. We found that CIP2A down-regulation increased apoptosis to very small extent so that it cannot be considered as synergistic effect as mediated by PME-1 depleted cells (FIG. 4C), supporting the idea that these effects are specific to PME-1 down-regulation. Effective downregulation of CIP2A and PME-1 by their respective siRNAs was verified by western blotting (FIG. 4D).

Then we also tested three recently identified chemical activators of PP2A, FTY720, Selenate and Xylulose-5-phosphate, for their ability to promote apoptosis in response to STS treatment. In order to facilitate the comparison between PME-1 siRNA transfected cells and the chemically treated cells, we first transfected T98G cells with Scr. siRNA followed by pre-treatment with chemical PP2A activators for 6 hrs and then treatment with STS for 24 hrs prior sub-G0/G1 analysis by FACS (FIG. 4D). None of these chemical PP2A activators were able to sensitize apoptosis in glioblastoma cells upon STS treatment.

All the above results highlight the requirement of down-regulation of PME-1 expression and consequent activation of selected PP2A complexes for sensitization of glioblastoma cells to STS mediated apoptosis.

Figure 5A:
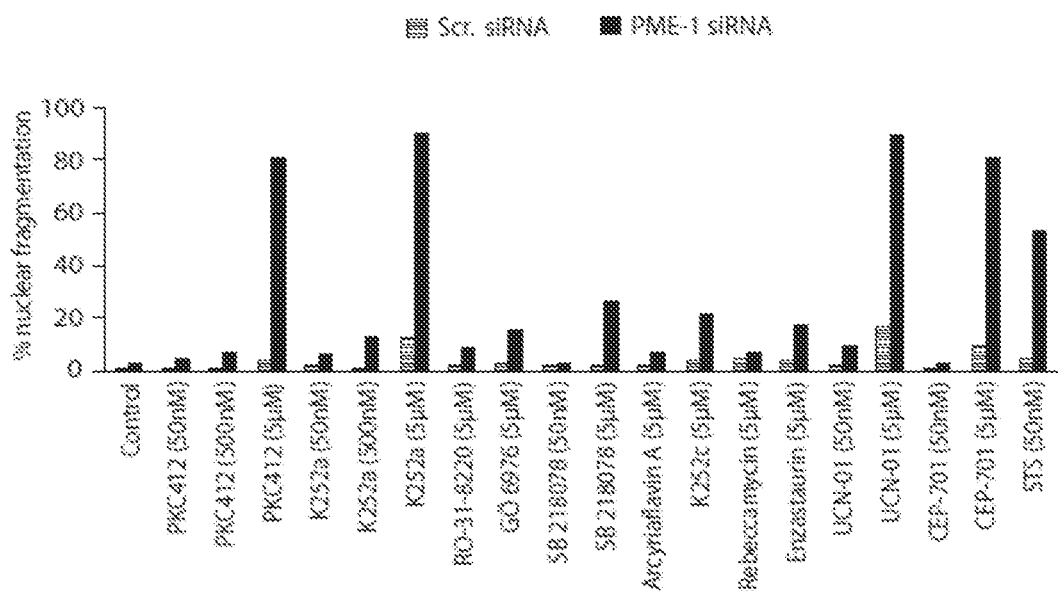
FIG. 5A shows the amount of apoptotic nuclear fragmentation in T98G glioblastoma cells after transfection with either scrambled or PME-1 specific dsRNA for 48 hours and treatment with indicated concentration of different staurosporine analogues/derivatives for another 24 hours.

Since STS has been documented in the literature to be a broadly specific inhibitor of kinases, it is considered less significant in the field of cancer chemotherapeutics. But, some STS derivatives are known which are far more specific and have fewer side effects and are currently in clinical trials for treatment of different diseases. So, we replaced STS with its derivatives, PKC412, K252a, RO-31-8220, GÖ 6976, SB 218078, Arcyriaflavin A, K252c, Rebeccamycin, Enzastaurin, UCN-01 or CEP-701 in our experimental setup at different concentrations (FIG. 5A). To our surprise, we found PKC-412, K252a, UCN-01 and CEP-701 being capable of inducing apoptosis in PME-1 depleted glioblastoma cells at levels even higher than STS itself. SB 218078 induced moderate levels of apoptosis at higher concentration. Whereas RO-31-8220 and the other tested STS derivatives were not active in these cells. The biochemical features, structure and potentiation to apoptosis of all these drugs in PME-1 depleted T98G cells are also listed in the Table 4.

Figure 5B:
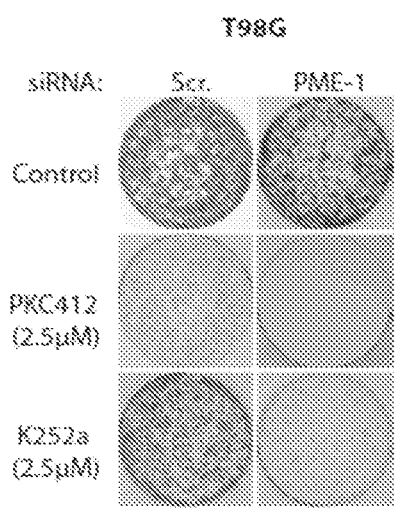
Figure 5C:
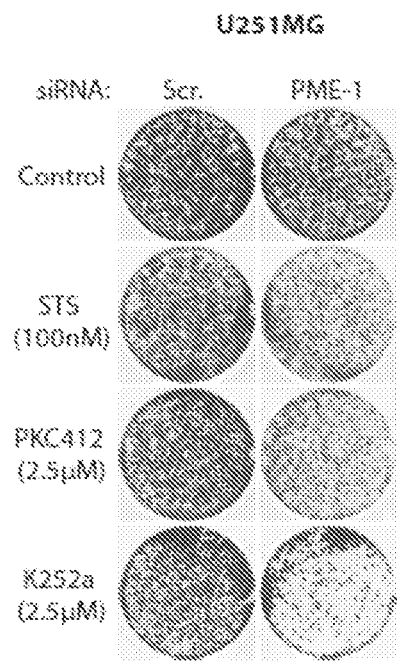
Figure 5D:
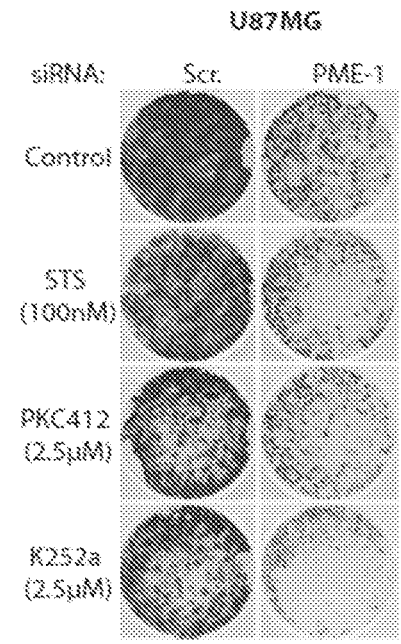

Colony formation assay in T98G cells using two active drugs, PKC412 and K252 also corroborate the above finding (FIG. 5B). In order to avoid the cell line specific effects, we also studied the efficacy of apoptosis sensitizing drugs, STS, PKC412 and K252a, in other PME-1 depleted glioblastoma cell lines U251MG and U87MG. In all studied cell lines, PME-1 depletion enhanced the cell killing activity of STS, PKC412, and K252a, although there was cell type dependent differencies in the efficacy of the treatment combinations (FIGS. 5C and 5D).

The invention claimed is:

1. A combination of at least one type of PME-1 silencing agent and a compound of Formula (I):

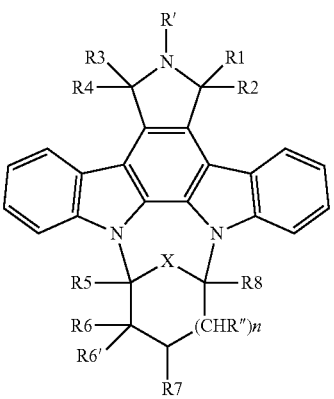

wherein
R' is H or alkyl;
R" is H or alkoxy;
R1 and R2 are H or together form oxo;
R3 and R4 are independently H, OH or together form oxo:
R5, R6, R6', R7, and R8 are independently selected from the group consisting of H, alkyl, alkoxy, hydroxy, hydroxylalkyl, alkoxycarbonyl, or mono- and dialkylamino;
X is $CH_2$ or O; and
n is 0 or 1,
wherein the PME-1 silencing agent comprises a nucleic acid sequence selected from the group consisting of SEQ ID NOs: 1 to 39, for use as a medicament.

2. The combination according to claim 1, wherein the PME-1 silencing agent is selected from the group consisting of an siRNA molecule, DsiRNA molecule, artificial miRNA precursor, shRNA molecule, antisense oligonucleotide, ribozyme, and agent preventing PME-1 function towards PP2Ac.

3. The combination according to claim 1, wherein the compound of Formula (I) is selected from the group consisting of

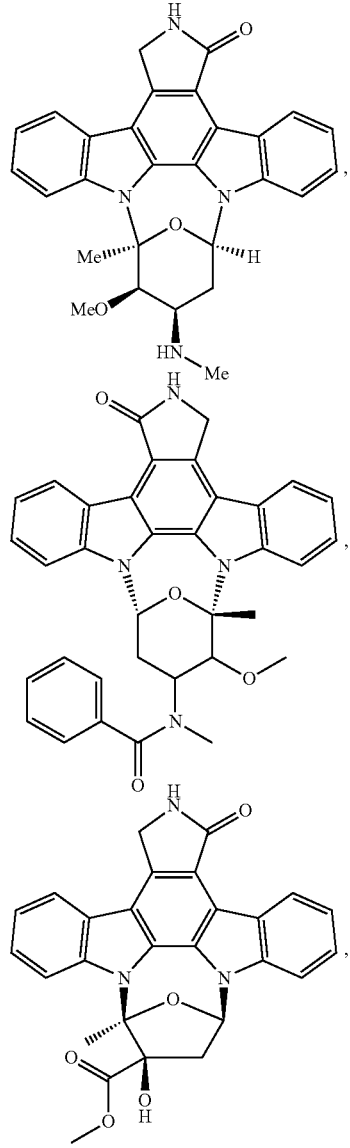

-continued

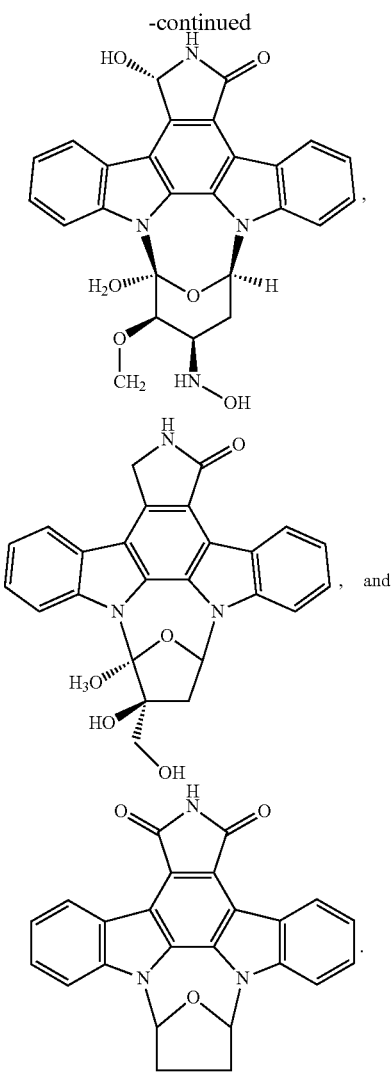
, and

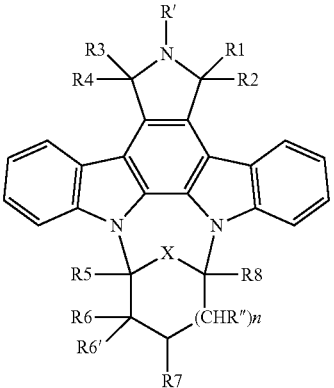
.

4. Small double-stranded RNA molecule comprising a nucleic acid sequence selected from a group consisting of SEQ ID NOs: 3 to 5.

5. A pharmaceutical composition comprising the combination according to claim 1, and at least one pharmaceutically acceptable carrier.

6. A method of treating a hyperproliferative disease in a human or animal subject in need of such treatment by administering at least one type of PME-1 silencing agent and a compound of Formula (I):

wherein
R' is H or alkyl;
R" is H or alkoxy;
R1 and R2 are H or together form oxo;
R3 and R4 are independently H, OH or together form oxo:
R5, R6, R6', R7, and R8 are independently selected from the group consisting of H, alkyl, alkoxy, hydroxy, hydroxylalkyl, alkoxycarbonyl, or mono- and dialkylamino;
X is $CH_2$ or O; and
n is 0 or 1,
wherein the PME-1 silencing agent comprises a nucleic acid sequence selected from the group consisting of SEQ ID NOs: 1 to 39, concomitantly, simultaneously, or subsequently to said subject.

7. The method according to claim 6, wherein the PME-1 silencing agent is selected from the group consisting of an siRNA molecule, DsiRNA molecule, artificial miRNA precursor, shRNA molecule, antisense oligonucleotide, ribozyme, and agent preventing PME-1 function towards PP2Ac.

8. The method according to claim 6 for use in the treatment of a hyperproliferative disease selected from the group consisting of psoriasis, myocardial hypertrophy, benign tumors, solid cancers and haematological cancers.

9. The method according to claim 8, wherein said solid cancer is selected from the group consisting of squamous cell carcinomas of the head and neck, colon cancer, gastric cancer, breast cancer, ovarian cancer, prostate cancer, cervical cancer, brain cancer, glioma, astrocytoma, and glioblastoma.

10. A pharmaceutical composition comprising the small double-stranded RNA according to claim 4, and at least one pharmaceutically acceptable carrier.

11. A combination of at least one type of PME-1 silencing agent and Midostaurin,
wherein the PME-1 silencing agent comprises a nucleic acid sequence selected from the group consisting of SEQ ID NOs: 1 to 39, for use as a medicament.

12. The combination according to claim 11, wherein the PME-1 silencing agent is selected from the group consisting of an siRNA molecule, DsiRNA molecule, artificial miRNA precursor, shRNA molecule, antisense oligonucleotide, ribozyme, and agent preventing PME-1 function towards PP2Ac.

13. A pharmaceutical composition comprising the combination according to claim 11, and at least one pharmaceutically acceptable carrier.

14. A method of treating a hyperproliferative disease in a human or animal subject in need of such treatment by administering at least one type of PME-1 silencing agent and Midostaurin,
wherein the PME-1 silencing agent comprises a nucleic acid sequence selected from the group consisting of SEQ ID NOs: 1 to 39, concomitantly, simultaneously, or subsequently to said subject.

15. The method according to claim 14, wherein the PME-1 silencing agent is selected from the group consisting of an siRNA molecule, DsiRNA molecule, artificial miRNA precursor, shRNA molecule, antisense oligonucleotide, ribozyme, and agent preventing PME-1 function towards PP2Ac.

16. The method according to claim 14 for use in the treatment of a hyperproliferative disease selected from the group consisting of psoriasis, myocardial hypertrophy, benign tumors, solid cancers and haematological cancers.

17. The method according to claim 16, wherein said solid cancer is selected from the group consisting of squamous cell carcinomas of the head and neck, colon cancer, gastric cancer, breast cancer, ovarian cancer, prostate cancer, cervical cancer, brain cancer, glioma, astrocytoma, and glioblastoma.

* * * * *